(12) United States Patent
Ganter et al.

(10) Patent No.: US 11,147,745 B2
(45) Date of Patent: Oct. 19, 2021

(54) AUTOMATED ENTERAL NUTRITION

(71) Applicant: AXIUM MTECH SA, Nyon (CH)

(72) Inventors: Christoph Ganter, Zurich (CH);
Michael Jedwab, Lausanne (CH);
Dorion Benjamin, Martigny (CH);
Natalia Muehlemann, Territet (CH);
Eric Johnson, Long Lake, MN (US);
Steven Bernard, Eden Prairie, MN (US)

(73) Assignee: AXIUM MTECH SA, Nyon (CH)

( * ) Notice: Subject to any disclaimer, the term of this patent is extended or adjusted under 35 U.S.C. 154(b) by 290 days.

(21) Appl. No.: 16/331,580

(22) PCT Filed: Sep. 8, 2017

(86) PCT No.: PCT/EP2017/072557
§ 371 (c)(1),
(2) Date: Mar. 8, 2019

(87) PCT Pub. No.: WO2018/046646
PCT Pub. Date: Mar. 15, 2018

(65) Prior Publication Data
US 2019/0216688 A1    Jul. 18, 2019

Related U.S. Application Data

(60) Provisional application No. 62/385,650, filed on Sep. 9, 2016, provisional application No. 62/425,344, filed
(Continued)

(51) Int. Cl.
*A61J 15/00*    (2006.01)
*G16H 20/17*    (2018.01)
(Continued)

(52) U.S. Cl.
CPC ....... *A61J 15/0011* (2013.01); *A61J 15/0084* (2015.05); *A61M 5/16827* (2013.01);
(Continued)

(58) Field of Classification Search
CPC ...... A61M 2005/14208; A61M 5/16877; A61J 15/0076; A61J 15/0084; A61J 15/0088
See application file for complete search history.

(56) References Cited

U.S. PATENT DOCUMENTS 10,682,288 B1 *   6/2020   Elia ..................... A61B 5/4211
2014/0031784 A1   1/2014   Flynn et al.
(Continued)

FOREIGN PATENT DOCUMENTS

WO    2015184366    12/2015

*Primary Examiner* — Emily L Schmidt
(74) *Attorney, Agent, or Firm* — K&L Gates LLP

(57) ABSTRACT

A system can automatically adjust flow rates/feeding regimen of a feeding pump feeding fluids/enteral nutrition to a patient. The system can, based upon a prescribed volume of nutrition or nutritional targets (such as and not limited to energy (calories), protein etc.) to be delivered and a prescribed delivery duration, adjust the pump flow rate/feeding regimen following unexpected delivery interruptions to achieve at or near to the prescribed total volume/nutritional targets to be delivered, despite the interruptions.

14 Claims, 9 Drawing Sheets

Related U.S. Application Data on Nov. 22, 2016, provisional application No. 62/431,704, filed on Dec. 8, 2016.

(51) Int. Cl.
　　　*G16H 20/60*　　　(2018.01)
　　　*A61M 5/168*　　　(2006.01)
　　　*A61M 5/172*　　　(2006.01)

(52) U.S. Cl.
　　　CPC .............. *G16H 20/17* (2018.01); *G16H 20/60* (2018.01); *A61J 15/0076* (2015.05); *A61J 15/0092* (2013.01); *A61M 5/1723* (2013.01)

(56) References Cited

U.S. PATENT DOCUMENTS

| | | |
|---|---|---|
| 2015/0065988 A1 | 3/2015 | Holderle et al. |
| 2015/0343141 A1* | 12/2015 | Lindo ............... A61M 5/16827 604/500 |
| 2016/0074573 A1* | 3/2016 | Kohlbrecher ......... A61M 5/142 604/500 |
| 2020/0281819 A1* | 9/2020 | Elia ..................... A61J 15/0084 |

* cited by examiner

AUTOMATED ENTERAL NUTRITION

CROSS REFERENCE TO RELATED APPLICATIONS

The present application is a National Stage of International Application No. PCT/EP2017/072557, filed on Sep. 8, 2017, which claims priority to U.S. Provisional Patent Application No. 62/385,650, filed on Sep. 9, 2016, U.S. Provisional Patent Application No. 62/425,344, filed on Nov. 22, 2016, and U.S. Provisional Patent Application No. 62/431,704, filed on Dec. 8, 2016, the entire contents of which are being incorporated herein by reference.

BACKGROUND

The present disclosure relates generally to devices and methods for administering multiple fluids such as enteral feeding solutions. More specifically, the present disclosure is directed to a system and method for improving nutrition delivery by automation.

When a patient is unable to eat normally, an infusion set can provide an enteral solution containing nutrition and optional medication to the patient. The infusion set can be used with a pump (e.g., a peristaltic pump) to regulate the amount and the rate at which the enteral solution is delivered from a reservoir to the patient.

Typically the amount of enteral solution administered to the patient must be precisely controlled, especially if the enteral solution contains potent compounds. In many enteral feeding systems, the engagement of the tube to a peristaltic pump controls the flow of fluid to the patient according to the speed of the peristaltic pump. Nevertheless, excess fluid can reach the patient due to gravity, which is known as free-flow and is not only undesirable but can be dangerous. Just as a free-flow condition due to gravity can be dangerous, pump flow rate speeds exceeding certain thresholds are undesirable as well.

Certain patients and patient settings require continuous enteral nutrition, which can be delivered according to a prescription. Current systems drive the prescriptions according to a set flow rate and a set period of time to achieve a desired total volume. For various reasons, continuous enteral nutrition delivery can be interrupted and, as a result, the pump paused. However, a drawback of pausing the pump during a continuous enteral nutrition of current systems is that the prescription may not be fully completed due to pumping time lost during the interruption.

Prescription fulfillment can also be affected by variations in the flow rate accuracy of the enteral pumping system. Enteral pumping systems are typically rated for an accuracy of +/−5 to 10%. This range may be even wider depending on the configuration of the pumping system. Accuracy variations are affected by factors such as the nutrition viscosity, the nutrition container head height, the feeding tube size, and the physical properties of the enteral tubing set.

SUMMARY

The present disclosure provides a continuous or intermittent enteral nutrition delivery system and method that allows a user or clinician to input a desired delivery volume or prescription, such as nutrition targets (e.g., energy or calories), into a pump which calculates a flow rate and other parameters (such as remaining volumes and energy deficit) accordingly. Unlike current systems which are flow-rate driven, the system of the present disclosure is generally volume and/or nutrition target driven. Specifically, the present disclosure enables a user or clinician to specify a volume or nutrition target to be delivered during a nutrition delivery, a period of time to during which that volume/nutrients must be delivered, and (where appropriate) maximum tolerated rates/bolus amounts. In such an embodiment, the flow rate of the pump or other nutrition regimen (e.g. in case of intermittent feeding) is calibrated automatically to achieve the nutrition targets, volume and duration parameters. It should be appreciated that in various other embodiments disclosed herein, while one of the intents is to define the total volume in a given time, the pump can alternatively accept an input of one or more of a combination of volume, flow rate, or time/duration of delivery. The calibration includes a request for confirmation by a clinician before starting delivery to confirm flow rates tailored to each patient individually. By operating as a target-driven (e.g., but not limited to volume-driven or calorie-driven) nutrition delivery program, the present disclosure provides a system that allows a user or clinician to, during nutrition delivery, pause the infusion and the system calculates a catch-up flow rate or delivery regimen (e.g., but not limited to catch-up or intermittent regimen) to still achieve a 100% delivery according to the prescription despite the infusion interruption (or as close as possible to 100% considering the maximum delivery rates and individual patient tolerance).

It should be appreciated that, depending upon the duration of interruption, the new calculated catch-up flow rate may exceed a safe flow rate limitation of the pump or maximum tolerance threshold rate specified by a clinician. In various embodiments, the system provides an indication of whether the calculated catch-up flow rate falls outside of the pump limits or tolerance threshold. If the calculated catch-up flow rate falls outside of pre-set pump or threshold limits, the system calculates and displays a revised delivery percentage under the optimal 100%, and automatically sets or proposes a new flow rate to safely achieve the revised delivery percentage. As discussed in greater detail below, the system of one embodiment calculates and displays a revised over-delivery percentage of more than 100% to prepare to ameliorate a future predicted interruption.

Accordingly, in a general embodiment, the present disclosure provides a pump with control means for delivering an enteral nutritional composition, the pump having a drive functionally connected to a controller. The controller and pump are adapted to receive a target volume or nutrition targets of a first total volume of the composition to be delivered in a defined first time period. Based on the first volume and the first time period, the pump calculates a first delivery rate or delivery regimen (e.g., for intermittent use). Upon the occurrence and the duration of any external or internal delivery rate or regimen modifying event (e.g., interruption or pause in delivery), the controller with the pump recalculates an adapted second delivery rate/nutrition regimen at the end of the external or internal delivery rate modifying event, based on the residual volume/nutrition targets of the first volume/nutrition targets and the remaining time from the end of the external or internal delivery rate/regimen modifying event to the end of the first time period. Following the calculation of the adapted second delivery rate/regimen, the nutritional delivery continues with the adapted second delivery rate/regimen. In one embodiment, the pump is configured based upon a caloric density (e.g., in kcal/ml) of the first nutrition target.

An advantage of one or more embodiments provided by the present disclosure is to enable the interruption or pausing of an enteral nutrition delivery while automatically modifying flow rate and delivery regimens to achieve the goals of the original prescription.

Another advantage of one or more embodiments provided by the present disclosure is to calculate a catch-up flow rate and delivery regimens following a delivery interruption, wherein the pump flow rate is increased to meet the prescription despite the pause in delivery. In various embodiments, the catch-up flow rate/changes in nutrition regimen are displayed to the user or clinician.

Another advantage of one or more embodiments provided by the present disclosure is to determine whether or not a maximum catch-up flow rate following a delivery interruption is sufficient to deliver 100% of the prescribed nutrition within the planned treatment time.

An advantage of one or more embodiments provided by the present disclosure is, if the maximum catch-up flow rate/feeding regimen following delivery interruption is not sufficient to deliver 100% of the prescribed nutrition within the planned treatment time, to calculate the reduced percentage of prescription projected to be delivered and display that reduced percentage of prescription to the user or clinician.

Another advantage of one or more embodiments provided by the present disclosure is, if an interruption is predicted to likely occur during a delivery, setting the pump to a preemptive delivery flow rate in which the pump's flow rate is higher than that of the prescribed flow rate before any interruptions occur. In such an embodiment, prior to an interruption, the patient receives more nutrition than prescribed, creating an over-delivery buffer against which any interruption can be offset. It should be appreciated that, some embodiments use both a preemptive pump flow rate and a catch-up flow rate together to ensure safe delivery of the prescribed nutrition even when disrupt delivery.

Another advantage of one or more embodiments provided by the present disclosure is the integration of the pump with a central server over a hospital network, where the pump engages in bidirectional communication with the central server to incorporate into the feeding therapies patient-specific prescriptions, flow rate/feeding regimen calculations, and pump and patient tolerance flow rate limitations.

The present disclosure provides a pump system for delivering an enteral nutrition composition, the pump system comprising a pump, an input device, a controller, a memory device and a processor. Referring now to FIG. 7, the processor is configured to execute instructions stored on the memory device to cause the controller to: via the input device, enable a user to input a first nutrition parameter and a first duration of a nutrition delivery (T1), wherein the first nutrition parameter is a first nutrition volume to be delivered (V1). The controller calculates a first delivery flow rate (F1) of the pump based upon the first nutrition volume (V1) and the first duration (T1), starts the pump according to the first delivery flow rate (F1), and stops the pump in the event of a pump interruption of a second duration (I). Further, the controller, after the conclusion the pump interruption, calculates a partial nutrition volume delivered (V2) and a remaining nutrition volume to be delivered (V3), wherein: V1=V2+V3. The controller also calculates a partial time duration completed (T2) and a remaining time duration (T3), wherein T1=T2+T3. The controller also calculates a proposed delivery flow rate (F2) of the pump based upon the remaining nutrition volume to be delivered and the remaining time duration.

In an embodiment, the proposed delivery flow rate (F2) of the pump is higher than the first delivery flow rate (F1) of the pump.

In an embodiment, the instructions include a maximum allowable flow rate of the pump.

In an embodiment, the processor is configured to execute the instructions stored on the memory device to cause the controller to determine if the proposed delivery flow rate exceeds the maximum allowable flow rate.

In an embodiment, if the proposed delivery flow rate does not exceed the maximum allowable flow rate, the controller resumes the pump according to the proposed delivery flow rate.

In an embodiment, if the proposed delivery flow rate exceeds the maximum allowable flow rate, the controller resumes the pump according to the maximum allowable flow rate and the controller prompts the user for an input to reconfirm or modify the maximum allowable flow rate.

In an embodiment, a total nutrition volume delivered (VT) according to the maximum allowable flow rate for the remaining time duration is less than the first nutrition volume to be delivered (V1).

In an embodiment, the processor is configured to calculate a net shortage nutrition volume (VS), where VS=V1−VT, and a ratio (R) of total nutrition volume delivered and first nutrition volume to be delivered, where R=VT/V1.

Another embodiment includes a display device operable with the pump, the input device, the controller, the memory device, and the processor, wherein the processor is configured to display the net shortage nutrition volume on the display device.

In an embodiment, the processor is configured to display the ratio (R) on the display device.

In an embodiment, the first nutrition parameter to be delivered is a first nutrition energy target to be delivered (E1) or a first nutrition protein target to be delivered (P1).

Another embodiment includes, via the input device, enabling a user to input a caloric density (F1) of: the first nutrition energy target to be delivered (E1) and/or the first nutrition protein target to be delivered (P1).

Another embodiment includes calculating a first delivery flow rate of the pump based upon one or more of: the first nutrition energy target to be delivered (E1), the first nutrition protein target to be delivered (P1), and the caloric density (F1) of the first nutrition energy target to be delivered (E1) and/or the first nutrition protein target to be delivered (P1).

Another embodiment includes, after the conclusion of the pump interruption, calculating a partial nutrition energy (E2) or another predefined nutrition target, and calculating a remaining nutrition energy (E3) or another predefined nutritional target to be delivered, wherein E1=E2+E3.

Another embodiment includes, after the conclusion of the pump interruption, calculating a partial nutrition protein (P2) to be delivered and calculating a remaining nutrition protein (P3) to be delivered, wherein P1=P2+P3.

Another embodiment includes calculating a proposed nutrition regimen for intermittent feeding.

In an embodiment, intermittent feeding parameters exceed a pre-defined feeding parameter.

In an embodiment, the instructions include maximum allowed intermittent feeding parameters.

In an embodiment, the processor is configured to execute the instructions stored on the memory device to cause the controller to determine if the proposed delivery flow rate exceeds the maximum allowed intermittent feeding parameters.

In an embodiment, if the proposed delivery flow rate exceeds the maximum allowed intermittent feeding parameters, the controller prompts the user for input to reconfirm or modify the maximum allowed intermittent feeding parameters.

In an embodiment, a total nutrition energy delivered (ET) or total nutrition protein delivered (PT) according to the maximum allowable flow rate for the remaining time duration is less than the first nutrition energy delivered (E1) or the first nutrition protein delivered (P1), respectively.

In an embodiment, the processor is configured to calculate: a net shortage nutrition energy (ES) where $ES=E1-ET$ and an energy ratio (ER) of total nutrition energy delivered and first nutrition energy to be delivered, where $ER=ET/E1$; and/or a net shortage nutrition protein (PS) where $PS=P1-PT$ and a protein ration (PR) of total nutrition protein delivered and first nutrition protein to be delivered, where $PR=PT/P1$.

In an embodiment, the processor is configured to calculate daily and cumulative net shortage nutrition target deficits based upon one or more of: volume, energy, protein, or another predefined nutritional target.

Another embodiment includes a display device operable with the pump, the input device, the controller, the memory device, and the processor, wherein the processor is configured to display the daily and cumulative net shortage nutrition target deficits on the display device.

In an embodiment, the processor is configured to display the respective ratio (ER, PR) on the display device.

Another embodiment discloses a method for controlling a pump for delivering an enteral nutritional composition. The method comprises the steps of: receiving a first nutrition parameter and a first duration of nutrition delivery (T1) defining at least a portion of a prescription, wherein the first nutrition parameter is a first nutrition volume to be delivered (V1); starting the pump with a first delivery flow rate calculated based upon V1 and T1 of the prescription; stopping the pump in the event of a pump interruption of a second duration. After the second duration, calculate a proposed delivery flow rate based upon a duration of partial time remaining (TR) from the first duration of nutrition delivery of the prescription and a partial volume of the nutrition delivered (VR) from the first nutrition volume of the prescription.

Another embodiment of the method comprises the steps of determining if the proposed delivery flow rate exceeds a maximum allowable flow rate of the pump.

In another embodiment of the method, if the proposed delivery flow rate exceeds the maximum allowable flow rate, restarting the pump after the interruption has concluded at the maximum allowable flow rate for the duration of partial time remaining or until a subsequent interruption.

In another embodiment of the method, if the proposed delivery flow rate does not exceed the maximum allowable flow rate, restarting the pump after the interruption has concluded at the proposed delivery flow rate for the duration of partial time remaining or until a subsequent interruption.

In another embodiment of the method, the proposed delivery flow rate is calculated to enable the pump to deliver the first nutrition volume within the first duration of nutrition delivery of the prescription notwithstanding the pump interruption.

In another embodiment of the method, the proposed delivery flow rate increases as the second duration of the pump interruption increases.

Another embodiment of the method includes calculating a net shortage nutrition volume (VS), where $VS=V1-VT$, and where VT is a total nutrition volume delivered (VT) according to the maximum allowable flow rate for the remaining time duration, and a ratio (R) of total nutrition volume delivered and first nutrition volume to be delivered, where $R=VT/V1$.

Another embodiment of the method includes displaying, on a display device associated with the pump, the net shortage nutrition volume (VS).

Another embodiment of the method includes displaying, on a display device associated with the pump, the ratio (R).

In an embodiment of the method, the first nutrition parameter is a first nutrition energy target to be delivered (E1) or a first nutrition protein target to be delivered (P1).

In an embodiment of the method, the first delivery flow rate is calculated based upon at least E1 and P1 of the prescription.

Another embodiment of the method includes calculating a proposed nutrition regimen for intermittent feeding.

Another embodiment of the method includes defining a maximum allowable flow rate of the pump.

Another embodiment of the method includes defining at least one maximum allowable intermittent feeding parameter.

Another embodiment of the method includes defining at least one minimum allowable intermittent feeding parameter.

Another embodiment of the method comprises the steps of determining if the proposed intermittent regimen exceeds the at least one maximum allowable intermittent feeding parameter.

In an embodiment of the method, the at least one maximum allowable intermittent feeding parameter can be modified by a user.

The present disclosure also provides a non-transitory machine-readable storage medium comprising machine-readable instructions for causing a processor to execute a method for use with a medical device and an associated pump to automate enteral nutrition delivery. The method comprises receiving a first nutrition parameter and a first duration of nutrition delivery (T1) defining at least a portion of a prescription, wherein the first nutrition parameter is a first nutrition volume to be delivered (V1). The method further comprises starting the pump at a first delivery flow rate calculated based upon V1 and T1 of the prescription and stopping the pump in the event of a pump interruption of a second duration. The method further comprises, after the second duration has concluded, calculate a proposed delivery flow rate based upon a duration of partial time remaining (TR) from the first duration of nutrition delivery of the prescription and a partial volume of the nutrition delivered (VR) from the first nutrition volume of the prescription. The method further comprises comparing the proposed delivery flow rate with a maximum allowable flow rate, and if the proposed delivery flow rate exceeds the maximum allowable flow rate: restarting the pump at the maximum allowable flow rate and calculating and displaying the maximum allowable flow rate on a display device associated with the pump. If the proposed delivery flow rate does not exceed the maximum allowable flow rate, restarting the pump at the proposed delivery flow rate.

In another embodiment of the non-transitory machine-readable storage medium, the first nutrition parameter is a first nutrition energy target to be delivered (E1).

In another embodiment of the non-transitory machine-readable storage medium comprises the step of defining an energy density of the prescription.

In another embodiment of the non-transitory machine-readable storage medium, the first nutrition parameter is a first nutrition protein target to be delivered (P1).

In another embodiment of the non-transitory machine-readable storage medium comprises the step of defining a protein ratio of the prescription.

In another embodiment of the non-transitory machine-readable storage medium comprises the step of defining at least one maximum allowed intermittent feeding parameter.

In another embodiment of the non-transitory machine-readable storage medium, all of the maximum allowable flow rate and the at least one maximum allowed intermittent feeding parameter can be modified by a user. In an embodiment, the present disclosure provides a pump system for delivering an enteral nutrition composition, the pump system comprising a pump, an input device, a controller, a memory device and a processor. The processor is configured to execute instructions stored on the memory device to cause the controller to receive a first nutrition prescription including a first duration of a nutrition delivery and a first nutrition volume to be delivered and calculate a first delivery flow rate of the pump based upon the first nutrition volume and the first duration. The controller is further configured to receive an anticipated interruption input associated with a likely nutrition delivery interruption during the first duration of nutrition delivery, calculate a preemptive delivery flow rate of the pump based at least upon the first delivery flow rate and the anticipated interruption input, and start the pump according to the preemptive delivery flow rate.

In an embodiment, the anticipated interruption input includes an anticipated interruption duration.

In an embodiment, the controller is further configured to receive a second anticipated interruption input associated with a second likely nutrition delivery interruption, the second anticipated interruption input including a second anticipated interruption duration.

In an embodiment, the preemptive delivery flow rate is calculated based at least upon the first delivery flow rate, the anticipated interruption input, and the second anticipated interruption input.

In an embodiment, the preemptive delivery flow rate increases as the anticipated interruption duration increases.

In an embodiment, the preemptive delivery flow rate increases as the sum of the anticipated interruption duration and the second anticipated interruption duration increases.

In an embodiment, the preemptive flow rate is higher than the first delivery flow rate.

In another embodiment, the present disclosure provides a pump system for delivering an enteral nutrition composition, the pump system comprising a pump, an input device, a controller, a memory device and a processor. The processor is configured to execute instructions stored on the memory device to cause the controller to, via the input device, enable a user to input a first nutrition parameter and a first duration of a nutrition delivery (T1), wherein the first nutrition parameter is a first nutrition volume to be delivered (V1). The controller calculates a first delivery flow rate of the pump based upon the first nutrition volume (V1) and the first duration (T1) and starts the pump according to the first delivery flow rate. In the event of a pump interruption of an interruption duration, the system determines if the interruption duration exceeds an interruption duration threshold. If the interruption duration does not exceed the interruption duration threshold, the system continues operating the pump according to the first delivery flow rate. If the interruption duration exceeds the interruption duration threshold and after the conclusion the pump interruption, the system calculates: a partial nutrition volume delivered (V2) and a remaining nutrition volume to be delivered (V3), wherein: V1=V2+V3; a partial time duration completed (T2) and a remaining time duration (T3), wherein T1=T2+T3; and a proposed delivery flow rate of the pump based upon the remaining nutrition volume to be delivered and the remaining time duration.

In an embodiment, the controller is configured to, if the interruption duration does not exceed the interruption duration threshold, and in the event of an Nth pump interruption of an Nth interruption duration, determine if the sum of the interruption duration and the Nth interruption duration exceeds the interruption duration threshold.

In an embodiment, the operation of the pump is continued and the proposed delivery flow rate is not computed until the sum of the interruption duration and the Nth interruption duration exceeds the interruption duration threshold.

In an embodiment, the pump interruption is an occlusion.

In an embodiment, the pump interruption is a detection of an abnormality in the nutrition delivery or due to an air-in-line alarm.

One embodiment is directed to a pump has control means for delivering an enteral nutritional composition and a drive functionality connected to the control means. The control means are adapted to: receive a target volume of a first total volume of the composition to be delivered in a defined first time period and start the delivery with a first deliver rate calculated on the basis of the first volume and the first time period. The control means are further adapted to be supplied with the occurrence and the duration of any external or internal delivery rate modifying event, especially a stop of the delivery and to recalculate an adapted second delivery rate at the end of the external or internal delivery rate modifying event, based on the residual volume of the first volume and the remaining time from the end of the external or internal delivery rate modifying event and the end of the first time period. After recalculation of the adapted second delivery rate, the control means instructs the drive functionality to continue the delivery with the adapted second delivery rate.

In an embodiment, the external or internal delivery rate modifying event is a pausing of the delivery by an external or internal stop or pause command.

One embodiment includes a method for controlling a pump for delivering an enteral nutritional composition, comprising several steps. The steps include receiving a target volume of a first volume of the composition to be delivered in a defined first time period, and starting the delivery with a first delivery rate calculated on the basis of the first volume and the first time period. The steps further include receiving the occurrence and the duration of any external or internal delivery rate modifying event, especially a stop of the delivery and recalculating an adapted second delivery rate at the end of the external or internal delivery rate modifying event based on the residual volume of the first volume and the remaining time from the end of the external or internal delivery rate modifying event to the end of the first time period. After recalculation the method continues the delivery with the adapted second delivery rate. In an embodiment, a controller for a pump is programmed to execute the method. In an embodiment, a computer software program product is configured to execute the method when run on a computing device functionally connected to a pump.

One embodiment includes a method for controlling a pump for delivering an enteral nutrition composition, comprising several steps. Referring now to FIG. 8, the steps include receiving a first nutrition parameter and a first duration of a nutrition delivery (T1), wherein the first nutrition parameter is a first nutrition volume to be delivered (V1). The controller calculates a first delivery flow rate (F1) of the pump based upon the first nutrition volume (V1) and the first duration (T1), starts the pump according to the first delivery flow rate (F1), and stops the pump in the event of a pump interruption of second duration (I). Further, the controller, after the conclusion of a pump interruption, calculates a partial nutrition volume delivered (V2), a catch-up volume (V4) and a residual volume to be delivered (V5), wherein V1=V2+V4+V5. The controller also calculates a partial time duration completed (T2) and a catch-up time (T4) and a residual time duration (T5), wherein T1=T2+T4+T5. The controller also calculates a proposed delivery flow rate (F2) of the pump based upon a maximum allowable catch-up flow rate restriction. The controller also determines a residual flow rate (F3).

In an embodiment, the controller calculates the residual flow rate (F3) based upon the residual volume (V5) and the residual time (T5), wherein F3=V5/T5.

In an embodiment, the residual flow rate (F3) is equal to the first delivery flow rate (F1).

In an embodiment, the proposed delivery flow rate (F2) is greater than the residual flow rate (F3).

In an embodiment, the proposed delivery flow rate (F2) is equal to the maximum allowable catch-up flow rate restriction.

In an embodiment, the catch-up time T4=[V1−V2−F1*(T1−T2)]/(F2−F1)

One embodiment includes a method for controlling a pump for delivering an enteral nutritional composition, comprising several steps. First, the pump system receives a first nutrition parameter and an allotted duration of nutrition delivery defining a prescription, wherein the first nutrition parameter is a first nutrition volume to be delivered. The pump system then starts the pump with a first delivery flow rate and stops the pump in the event of a pump interruption of a first duration. After the first duration, the pump system calculates a proposed delivery flow rate based upon: (1) a duration of partial time remaining from the allotted duration of nutrition delivery of the prescription; and (2) a partial volume of the nutrition delivered from the first nutrition volume of the prescription. The pump system then determines if the calculated proposed delivery flow rate is greater than a pre-programmed maximum allowable catch-up flow rate. If the calculated proposed delivery flow rate is greater than the pre-programmed maximum allowable catch-up flow rate, the pump system calculates a remaining nutrition volume to be delivered equal to the first nutrition volume to be delivered minus the partial volume of nutrition delivered and calculates a second duration of time equal to the remaining nutrition volume to be delivered divided by the maximum allowable catch-up flow rate.

In an embodiment, the pump system also provides an option to a user to extend the delivery of the enteral nutritional composition if the calculated proposed delivery flow rate is greater than the pre-programmed maximum allowable catch-up flow rate.

In an embodiment, if the user exercises the option to extend the delivery, the pump system runs the pump beyond the allotted duration of nutrition delivery to deliver the first nutrition volume of the prescription.

Additional features and advantages are described herein and will be apparent from the following Detailed Description and the Figures.

DETAILED DESCRIPTION

Figure 1:
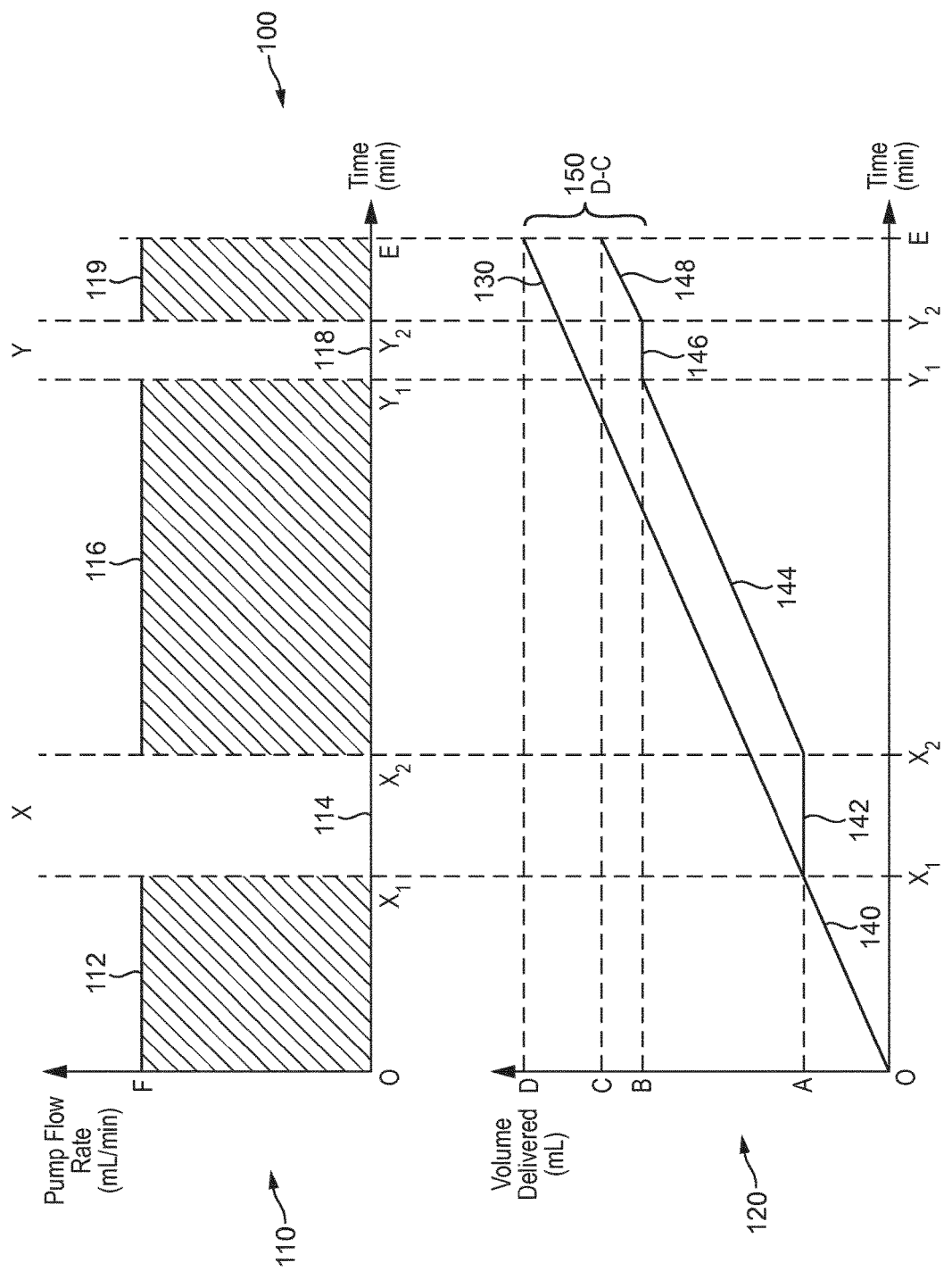
FIG. 1 shows flow rate and volume profiles of a prior art enteral nutrition system that undergoes interruptions or pauses in delivery.

As used in this disclosure and the appended claims, the singular forms "a," "an" and "the" include plural referents unless the context clearly dictates otherwise. Thus, for example, reference to "a fluid" or "the fluid" includes two or more fluids.

The words "comprise," "comprises" and "comprising" are to be interpreted inclusively rather than exclusively. Likewise, the terms "include," "including" and "or" should all be construed to be inclusive, unless such a construction is clearly prohibited from the context.

Nevertheless, the devices and apparatuses disclosed herein may lack any element that is not specifically disclosed. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

As used herein, "about" and "approximately" are understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number.

Enteral feeding pumps are devices that control the timing and the amount of nutrition delivered to a patient during enteral feeding. Enteral feeding is the administration of nutrient fluids to a patient who cannot eat via normal ingestion routes. Enteral administration typically occurs through a set of tubes between a feeding bag and a catheter inserted into the patient. A disposable cassette typically carries at least a portion of the tubing so that spent tubing may be easily disposed of.

Enteral feeding pumps can operate as part of a stand-alone nutrition delivery system or as part of a larger interconnected network of pumping apparatuses, controllers, servers, and databases. For various enteral feeding administrations, a doctor or clinician provides a prescription for an amount (e.g., volume, calories) and duration of continuous feeding or intermittent feeding regimen based upon the profile of each individual patient. It should be appreciated that various enteral feeding pump systems of the present disclosure are configured to enable the input of a feeding prescription, whether via a controller at the pump itself or a controller at a remote or separated server connected to the pump via a suitable network. In some embodiments, a controller associated with the pump is configured to operate the pumping speed, nutrition/enteral fluid delivery duration, and pumping timing based upon a variety of factors controllable by one or more of the patient, the clinician, indirectly by the prescription, and/or automatically by the pump controller.

In various embodiments of the present disclosure, an enteral feeding pump system includes an associated user interface or suitable display device (collectively hereinafter "user interface") that enables interaction between the patient or clinician and the pump system via a suitable associated input device. In various embodiments, a user or clinician, via the input device and user interface, has the ability to at least program the pump with pumping parameters, input a patient prescription, and monitor a continuous or intermittent enteral feeding pump delivery. It should be appreciated that such pump programming inputs may be achieved remotely according to known remote programming methods, as well as locally using an associated input device.

In various embodiments, a typical prescription for a pump system of the present disclosure defines at least one or more of: (1) a volume of nutrition to be delivered to the patient; (2) a flow rate profile controlling the rate of delivery of the nutrition to the patient; (3) a duration or time period during which the total nutrition is expected to be delivered to the patient; (4) energy prescribed to the patient; (5) protein or other macro/micronutrient prescribed per day over the determined period; and (6) type of nutrition (e.g., hyperproteinin or hypercaloric). In various embodiments with intermittent deliveries, a prescription could also include planned delivery stops (as discussed and illustrated in more detail below), planned interruptions, bolus feeds, and minimum and maximums on bolus feeds, maximum allowed intermittent feeding parameters, pre-planned interruption durations, flow rate, catch-up flow rate, and over-delivery flow rates. The embodiments discussed herein can be used not only for nutrition delivery, but also for hydration of a patient. For example, in various hydrating embodiments, the fluid delivered can be water or tea.

In various embodiments, the pump includes an interruption duration threshold, short of which, the pump does not go through the full recalibration and flow rate adjustment calculation and resetting described herein. For example, in one embodiment, if a delivery system experiences a plurality of minor pauses that are very short in duration (or pump interruptions), the feeding stops may not aggregate to a significant enough interruption to warrant recalculation of flow rates or total fluid delivered during the feeding. In various embodiments, the feeding stops, pauses, or pump interruptions may be upstream or downstream occlusions of the feeding lines, temporary power outages to the pump, or other abnormalities detected in the nutrition delivery, such as air detected in the feeding lines, short manual stoppage of the pump for any known reasons, pump errors causing a pause in delivery, or outputs from pump sensors indicating readings that exceed threshold safety values stored in the pump memory device.

It should be appreciated that, while an acceptable number of pump interruptions may be abbreviated enough in aggregate to not adversely affect the overall delivery, the pump system of various embodiments monitors the total interruption duration and compares it to a preset or a predefined threshold. In some embodiments, the predetermined threshold is a parameter of an inputted or calculated duration for the particular delivery. If, for example, the pump interruptions include a plurality of short occlusions or interruptions whose cumulative duration falls short of the predetermined threshold parameter, the pump continues with the feeding without adjustment or recalculation. If, on the other hand, the cumulative duration of the short occlusions or interruptions exceeds the predetermined threshold parameter (e.g., more than 1 or 2 minutes), the pump system recalculates flow rates to ensure accurate nutrition delivery in any of the manners described herein.

It should be appreciated that each of the above parameters can be defined directly by the operator via the prescription, or can be calculated directly or indirectly based upon one or more parameters or other variables. For example, in various embodiments, the volume to be delivered divided by the average flow rate of the pump will calculate the total duration of delivery. In various embodiments, the volume to be delivered can be calculated from information on the bar code or other suitable identification mechanism situated on the feeding bag or the product. In various embodiments the barcode can also inform the pump of the type of feed and display that information on the display device. It should be appreciated that, because the pump is informed of the type of feed, the display can update the user in real time of the accumulated parameters of the delivered feed, such as the amount of protein or calories.

During continuous enteral feeding, for various reasons, a patient may need to pause the nutrition delivery for a period of time. For example, enteral nutrition can be held or discontinued varying periods of time for diagnostic or therapeutic interventions undergo different procedures (including, but not limited to, bed side procedures, extubation/intubation, operating room procedures, or procedures in radiology suite). Patients may wish to be ambulatory away from the pump system, the reservoir or source of nutrition being fed to the patient may need replenishment, or the treatment may be interrupted for any other expected or unexpected reason, such as X-ray or other screening assessment. In various embodiments of the present disclosure, such a pause is enabled by instructing the controller to stop the pump via the suitable input device. Additionally, some embodiments include a controller that causes the pump to automatically interrupt nutrition delivery for various reasons.

During intermittent enteral feeding the prescription is subdivided over several feeding sessions with one or more planned delivery stops (as opposed to interruptions). Unexpected interruptions often disrupt intermittent feeding just as they do for continuous feeding. Therefore, it should be appreciated that the discussion herein of interruptions (expected or unexpected) can be remedied by the methods described for both intermittent and continuous feedings.

In the event of a nutrition delivery interruption, one or more of the defined pump parameters from the prescription will be affected, which could affect one or more of the calculated pump parameters. Therefore, an interruption in nutrition delivery may result in the failure to complete the prescription according to its intended requirements. For example, as most prior systems operate, if the pump flow rate is a defined parameter, and the total duration of the delivery is a defined parameter, an interruption will effectively result in a lower duration of active pumping time at the set pump flow rate, and therefore less than the intended total nutrition will be delivered to the patient. It is also possible (common case in current practice) that none of the pump parameters are affected (because most commonly used parameter is flow rate for continuous feeding) and when resuming delivery after pump pausing pump will continue delivery leading to under-delivery which may not be noticed in the absence of nutrition delivery monitoring (either in connection with information system or manually). Recent study across 160+ intensive care units ("ICUs") in many countries showed that on average only 60% of prescribed calories and protein are delivered to ICU patients. In the present disclosure, however, if the volume/nutrition targets and duration are both defined parameters and the flow rate is a calculated parameter, the automatic flow rate adjustment described herein (e.g., catch-up flow rate) enables the system to mitigate any deficiency of nutrition volume delivered to the patient in the event of an interruption.

Regardless of the reason for a pump interruption, the source causing the pump interruption, or which prescription parameters are defined and which are calculated, it should be appreciated that an interrupting event of any duration affects the volume/target of the total expected nutrition delivery as prescribed by the prescription. As discussed in greater detail below, one way to ameliorate the undesirable effects of a planned or unplanned delivery interrupting event is to cause the pump to adjust its flow rate (or feeding regimen for intermittent mode) to make up for the duration of the interruption without sacrificing the overall volume/calories to be delivered. For purposes of discussion, any adjustment of the flow rate or feeding regimen of the pump to compensate for pump down-time during an interruption or delivery pause will be referred to as a "catch-up flow rate". Typically, although not always, the catch-up flow rate is a higher rate than the programmed or calculated flow rate intended by the prescription for the nutrition administration. It should be appreciated that the catch-up flow rate, while typically being higher than the programmed flow rate, can also be subject to a pre-set maximum allowable catch-up flow rate restriction (pre-set parameters of intermittent regimen). Based upon one or more of the patient's condition, the patient's parameters and metrics, the nutrition profile, or any part of the enteral feeding prescription, the enteral feeding pump can be restricted to a maximum flow rate, beyond which neither the prescribed delivery flow rate nor the catch-up flow rate are allowed to exceed. It should be appreciated that the pre-set maximum allowable catch-up flow rate may differ from a pre-set maximum allowable prescribed flow rate. In various embodiments, the catch-up flow rate may vary from the pre-set flow rates.

In various embodiments, the volume/target of the total expected nutrition delivery as prescribed by the prescription is adjusted in anticipation of a potential interruption. Whether planned or unplanned, based upon past feedings, the presence of delivery interruptions can be predicted with a reasonable degree of likelihood. In such cases where a regimen will likely include an interruption, the pump can be programmed to adjust its flow rate higher before an interruption so that, when such an interruption occurs, the patient has already received excess nutrition compared with the programmed flow rate. Because the patient is ahead of schedule from the over-delivery, the anticipated interruption has an excess of nutrition from which to offset the nutrition shortage resulting from pump downtime, and the regimen more closely matches the prescription following the interruption. It should be appreciated that such an embodiment includes a preemptive increased flow rate, which is similar to a catch-up flow rate discussed above. By using a preemptive increased flow rate, the pump need not aggressively max out a catch-up flow rate following an interruption.

In various embodiments, the pump system is an adaptive pump system that is programmed to receive a variety of different inputs related to predicted interruptions. One such adaptive pump system proactively anticipates or predicts interruptions based upon the inputs (e.g., past interruptions typical to the particular patient, institution, facility, or clinician) and modifies the calculated pump delivery flow rate(s) similar to the preemptive increased flow rate discussed above. For example, in one such adaptive pump system embodiment, a hypothetical patient has in the past been typically disconnected for approximately 30 minutes at 10:00 am to be bathed and for the room to be cleaned. For the first few days of this consistent interruption, the adaptive pump system would record those interruptions and learn from those events to create an input and instruct the system to modify its preemptive flow rate in future deliveries to compensate for the likely 30 minute 10:00 am interruption. In one such situation, for example, the preemptive flow rate may need to be 10% higher to compensate for the planned 30 minute interruption and still achieve 100% of the feeding volume prescribed. It should be appreciated that, the more anticipated or predicted interruptions, and the longer the duration of the sum total of interruptions predicted, the higher preemptive flow rate adjustment made to the delivery.

The adaptive pump system of this and other embodiments avoids the potentially undesirable situation in which the patient falls short of the optimal 100% prescribed feeding volume delivered on account of an interruption that was wholly predictable. It should be appreciated that various adaptive pump systems of the current disclosure can incorporate any conceived number of inputs of known scenarios that may result in anticipated or predicted interruptions in a patient's feeding regimen.

It should be appreciated that, by using an associated memory device or data connection and the inputs regarding anticipated interruptions, the adaptive pump system of the present disclosure can also learn and track the likelihood of future interruptions actually occurring vs. those that were planned or budgeted in the modification of the preemptive flow rate. For example, if the above hypothetical 30 minute interruption were to occur three consecutive days at 10:00 am, the adaptive pump system of one embodiment would be able to assign a high degree of likelihood that the same interruption would occur on the fourth day as well. It should be appreciated that, as the accuracy of its predictions changes and the pump is dynamically updated based upon actual occurrences, the adaptive pump system can also adjust the preemptive flow rate associated with the predicted interruption accordingly. For example, if the likelihood of the 30 minute interruption at 10:00 am has decreased significantly, yet the interruption still has some chance of occurring, the adaptive pump system could automatically hedge the chance that the interruption occurs by reducing the preemptive flow rate to deliver only 5% more than prescription, rather than 10% more than prescription. It should be appreciated that various different factors can incorporated into the preemptive flow rate delivery modification.

In some adaptive pump system embodiments, the interruption prediction inputs which are tracked and modified are either patient-specific or institution-specific. It should be appreciated that the patient-specific inputs may be discerned from clinician or user-provided information as well as past data regarding interruptions experienced. The institution-specific inputs to the adaptive pump system may be affected by the nurse associated with the specific patient, the unit of the institution the patient is admitted into, or any other known hospital or institutional variables that may affect or interrupt a patient's feeding regimen.

It should be appreciated that, in various embodiments, the preemptive flow rate and catch-up flow rate can both be used together as well. For example, in one exemplary feeding regimen, if an interruption is long enough, even maxing out the catch-up flow rate following the interruption may not be sufficient to deliver the entire prescription. In such a case, employing a hybrid that also uses a preemptive flow rate increase would build up reserves of the nutrition delivered beyond that of the expected prescribed delivery, so that following the unusually long interruption, the catch-up flow rate (if necessary) can be set appropriately to deliver the full volume to the patient as prescribed.

In various embodiments the pump is programmed to deliver an intermittent rather than continuous feeding regimen. In such an embodiment, the system is programmed with maximum allowed intermittent feeding parameters. One such example includes parameters suggested by the pumps but requiring confirmation or modification by the user or clinician to account for individual patient tolerance, symptoms, and/or condition. As discussed in greater detail below, during an intermittent feeding regimen, a prescription could include pre-planned feeding stops of set durations. In various embodiments, a bolus feed is pre-planned at various stages of the delivery (both continuous and intermittent). In intermittent embodiments which bolus feeds are missed during a stop (planned or not), the planned duration of feeding stops can be decreased to achieve all boluses. Alternatively, if a bolus feed is missed, rather than adjusting the planned duration of the feeding stop, future bolus amounts could be increased to meet the total delivery. It should be appreciated that another alternative embodiment uses a combination of both methods to achieve full delivery: shortening stop duration and increasing future bolus amounts. For safety, a minimum bolus interval and a maximum bolus amount could be included in the prescription. It should be appreciated that a range of parameters could also be used to make up for the shortfall, such as time, flow rate, or caloric density.

In some embodiments, a doctor or clinician is granted permission to manually override any one of the maximum flow rate restrictions (e.g., pre-set maximum allowable catch-up flow rate and a pre-set maximum allowable prescribed flow rate and a pre-set maximum allowable preemptive flow rate). In one such embodiment, the system notifies the doctor or clinician that a pre-set by pump or by a clinician maximum flow rate has been reached, and provides the option to exceed the pre-set maximum flow rate. In an intermittent delivery embodiment, the doctor or clinician is granted permission to manually override any one of the minimum or maximum bolus feed amounts, planned stop duration, as well as the above-described flow rate restrictions.

In one embodiment, safety may be increased for a patient on insulin infusion by a mandatory validation (by a healthcare professional) of all changes of feed rates proposed by the pump system. Examples of such changes requiring validation are those that may have implication on insulin infusion.

While failing to complete a prescription is undesirable and should be avoided if possible, such situations are often times unavoidable when an interruption is long enough. In some situations, the pre-set maximum allowable catch-up flow rate is still insufficient to deliver the total prescribed nutrition within the prescribed delivery time. In such cases, it is beneficial to calculate and inform the user and/or clinician as to the percentage of partial prescription that will be completed within the delivery time frame prescribed. It may be resolved by changing prescription to higher calorie density enteral formula within the limits of the patient's tolerance.

For example, in one embodiment discussed in greater detail below, the duration of a delivery interruption exceeds the amount of time for which a maximum allowable catch-up flow rate could fully compensate within the prescribed delivery time. In such an instance, the pump system is configured to calculate and display a delivery status to the user including how much of the prescribed delivery can be delivered according to the maximum allowable catch-up flow rate. In various embodiments, the displayed delivery status includes a real-time updating percentage of how much of the prescribed nutrition will be delivered based upon varying flow rate profiles. Additionally, in various embodiments, the display device can include a status of a real-time updating percentage of how much prescribed nutrition has been actually delivered at that point in the feeding. It can also display daily or cumulated nutritional deficit (e.g., calorie or protein). As flow rates change throughout the enteral feeding delivery (whether the prescribed flow rate, the catch-up flow rate, or another transitional flow rate), the pump system is configured to automatically readjust and display the expected total delivery percentage or actual volume or calorie/other nutrient deficit expressed accordingly (e.g., kcal). The extrapolations calculated and displayed can be, but are not necessarily, linear based upon a first flow rate and a second catch-up flow rate. The real-time updated delivery percentage status can also be dynamically adjusted based upon a plurality of proposed flow rates vs. actual flow rates, taking into account ramp-up flow rates and actual nutrition volume delivered, rather than predicted nutrition volume delivered.

In one example embodiment, a prescription was not fully delivered within the prescribed delivery time, even when operating at the maximum allowable catch-up flow rate. When the pump system has resumed following an interruption, and the resumption is set at the maximum allowable catch-up flow rate, the system of one embodiment automatically extrapolates the maximum amount of nutrition that can be delivered in at the maximum allowable catch-up flow rate within the amount of time remaining in the prescription. The pump will provide an extended delivery option to achieve full prescription delivery.

For example, if after an interruption, the prescription is 80% delivered, the pump system will calculate that, even at the maximum allowable catch-up flow rate for the remainder of the delivery, the prescription will only be 90% delivered at the end of the allotted time. In such an embodiment, the pump system will calculate that the delivery will not hit 100% of the prescription within the allotted time and notify the patient or clinician accordingly. In one exemplary embodiment, the pump system provides an option to extend the time of the delivery by a calculated duration to achieve 100% delivery of the nutrition. In the embodiment discussed above, at the time of resumption of delivery following an interruption, the pump system can notify the patient that, although 80% of the delivery has been completed, even under the maximum allowable catch-up flow rate, only 90% can be delivered. However, if the patient or clinician is willing to extend the delivery time by a calculated duration of time, 100% of the nutrition can be delivered. It should be appreciated that the pump system can be configured to calculate the extended delivery duration based on an assumed maximum allowable catch-up flow rate, an override flow rate from a clinician, or any other suitable flow rate encountered during the delivery described herein. See FIG. 9 and the accompanying discussion below for an example embodiment of an extended delivery option to achieve full prescription delivery.

In an intermittent embodiment, also displayed and illustrated below, the duration of one or more planned delivery stops can be adjusted based upon unplanned interruptions. Additionally, the existence and duration of one or more planned delivery stops can affect the catch-up flow rate and the urgency which the system attempts to realign the feeding flow profile with that of its prescription. In other words, if an intermittent delivery has five planned stops, and after the first planned stop is 20% behind prescription due to unplanned interruptions, the system can readjust the catch-up flow rate to more conservatively reach 100% delivery by the end of all the feeding sessions than if there were only two planned stops. In the first five-stop scenario, after the first stop, the system knows there will be five more feeding sessions during which the relative 20% deficit can be compensated. In the second two-stop scenario, however, there are only two subsequent feeding sessions to make up for the 20% deficit at the time of the first stop. Therefore, the second scenario would require a more aggressive catch-up flow rate or over-delivery flow rate for the fewer remaining feeding sessions than the first scenario. It should be appreciated that, in each case, the intermittent delivery system could include an over-delivery flow rate planned into the prescription to target an early completion in the anticipation of interruptions or missed bolus feedings. Additionally, for both illustrative examples, the catch-up/over-delivery flow rates could be increased in conjunction with the stop duration being decreased as necessary to reach 100% delivery.

Referring now to FIG. 1, two charts illustrate the nutrition delivery profile of a typical prior art device. In this flow profile 100, the top chart 110 depicts pump flow rate vs. time. The bottom chart 120 depicts total volume delivered vs. time. The time units are continuous from the flow rate chart 110 to the volume delivered chart 120. It should be appreciated that the units discussed herein can be any suitable units for flow rate, volume, and time, and those depicted in the figures are merely exemplary. Dashed lines have been added to more easily identify volume, flow rate, and time thresholds at various points in the delivery (each alphanumerically labeled).

As seen in the flow profile 100, the delivery has a total duration of E minutes, and during that duration, delivery was interrupted twice, as illustrated by the dashed lines defining time period X and time period Y. The top chart 110 illustrates the initial pump flow rate F ml/min, which is programmed by the system according to a prescription. Flow rate line 112 shows that the pump continues a constant flow rate F from the beginning of delivery until the beginning of interruption X, marked at X1 minutes. When the delivery is interrupted at X1 minutes, the pump's flow rate goes from F ml/min to 0 ml/min, as depicted by flow rate line 114, which continues until the interruption X is over and the system resumes pumping, marked at X2 minutes.

It should be appreciated that, according to such a prior art delivery profile, because the prescription is flow-rate based, rather than volume-based, the flow rate of the pump is static and therefore resumes after an interruption as if the interruption never happened. As seen in chart 110, flow rate line 116 indicates that the pump is switched back on at the prescribed pump flow rate F ml/min after the X interruption concludes at time X2 minutes. The delivery in chart 110 continues until the second interruption Y begins, marked at Y1 minutes. Similar to the first interruption X, this second interruption Y results in the pump being switched off and flow rate going to 0 ml/min, as indicated by flow rate line 118, which continues until interruption Y is over and the system resumes pumping, marked at Y2 minutes. Again, because the prior art system illustrated is flow-rate driven, the pump resumes its flow rate F ml/min at flow rate line 119 until the conclusion of delivery at time E minutes.

Referring now to chart 120 of FIG. 1, the total volume delivered for the above-discussed prior art nutrition delivery profile is illustrated. The volume delivered in chart 120 is the mathematical integral of the flow rate profile of chart 110. Line 130 illustrated in chart 120 represents an ideal "best-fit" line that would be followed if the prescription is performed exactly as expected and without any issues.

When the pump operates at flow rate F ml/min at 112, the total volume delivered is illustrated on line 140. Upon the start of interruption X at time X1 minutes, the total volume ceases to accumulate 142 because the pump has stopped operating, and only after X2 minutes (and the conclusion of interruption X) does the total volume continue to rise along line 144. It should be appreciated that, because the flow rate 116 is still F ml/min, the slope of 144 is equal to the slope of 140, which is equal to F. Similar to interruption X, the interruption Y at Y1 minutes results an 0 ml of volume accumulating from Y1 to Y2 minutes 146. Following interruption Y, pumping resumes at F ml/min 119 and volume accumulates as expected until the delivery's conclusion at E minutes.

Chart 120 illustrates the deficiency of this prior art system at E minutes. Specifically, it should be appreciated that the difference in total volume delivered C ml vs. total volume prescribed D ml is shown by bracket 150. Because the interruptions stopped the pump, and the subsequent restarts of the pump did not account for the interruptions, D minus C ml 150 of nutrition that should have been delivered was not.

For each of the illustrated embodiments in FIGS. 2 to 6, the nutrition parameter defined is volume for ease of comparison with the prior art device of FIG. 1. As discussed throughout, it should be appreciated that it is contemplated for each embodiment that the nutrition parameter defined could instead or additionally be energy, protein, or any other appropriate parameter.

Figure 2:
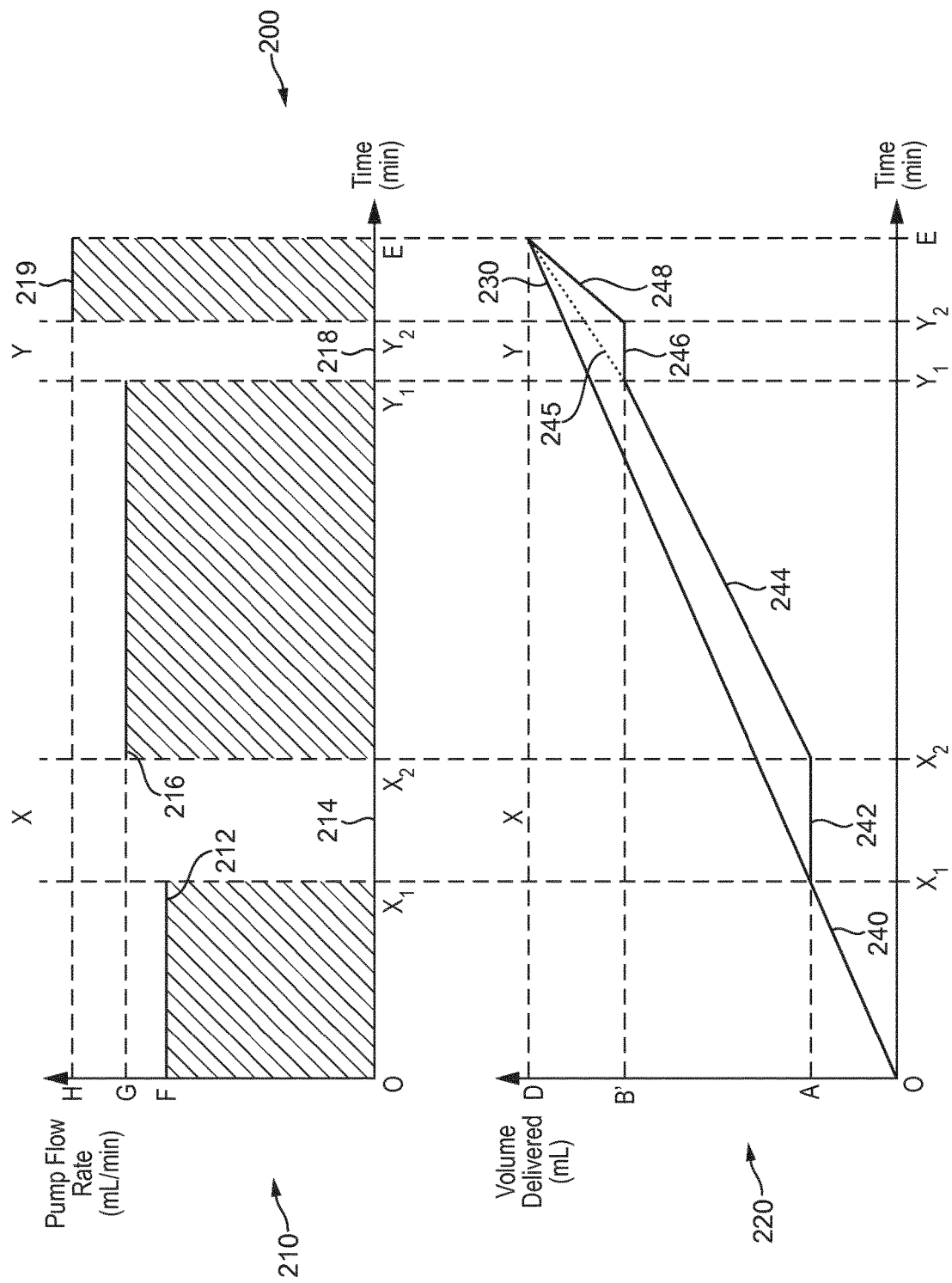
FIG. 2 shows flow rate and volume profiles of an automated enteral nutrition system of the present disclosure that undergoes interruptions or pauses in delivery, followed by catch-up flow rate adjustments.

Referring now to FIG. 2, two charts illustrate the nutrition delivery profile of one example nutrition delivery system of the present disclosure. Like FIG. 1, flow profile 200 includes a top chart 210 that depicts pump flow rate vs. time and a bottom chart 220 that depicts total volume delivered vs. time. As with FIG. 1, dashed lines have been added to more easily identify volume, flow rate, and time thresholds at various points in the delivery (each alphanumerically labeled).

To draw an analogous comparison to the FIG. 1 delivery, the FIG. 2 delivery likewise has a total duration of E minutes, and was interrupted twice, as illustrated by the dashed lines defining time period X and time period Y. The top chart 210 illustrates the initial pump flow rate F ml/min, which is programmed by the system according to a prescription. Flow rate line 212 shows that the pump continues a constant flow rate F from the beginning of delivery until the beginning of interruption X, marked at X1 minutes. When the delivery is interrupted at X1 minutes, the pump's flow rate goes from F ml/min to 0 ml/min, as depicted by flow rate line 214, which continues until the interruption X is over and the system resumes pumping, marked at X2 minutes.

Now referring to the bottom chart 220, the first portion of total volume delivered from the start of delivery to X1 240 is identical to profile 140 of FIG. 1. Following the interruption X, however, it should be appreciated that the total volume delivered 242 between time X2 minutes and Y1 minutes gets closer to the "best fit" prescription line 230. In order to increase the total volume delivered along 244, its slope is steeper to make up for the lost pumping time accounted for between X2 minus X1 minutes when the pumping was interrupted 242. As seen in upper chart 210, to make up for the loss in total volume delivered vs. total volume expected to be delivered as of time X2, the pump flow rate was increased to recalibrate and speed up to flow rate G ml/min. It should be appreciated that, as of the recalibration to G ml/min at line 216, the system is instructing the pump to speed up to a flow rate that will, between X2 min and the end of treatment at E min, result in the total volume delivered equaling the prescribed volume to be delivered. Reflected in lower chart 220, the slope of the volume delivered 244 is increased from F at 240, and calculated to intersect with the "best fit" prescription profile 230 at the end of treatment E, as illustrated by phantom dotted line 245, the slope of which equals G. It should be appreciated that in this embodiment, the system does not know to expect the timing, existence, or duration of another interruption, and therefore must program the flow rate increase to behave as if the pump will not be interrupted again and deliver the correct amount of prescribed volume D by the prescribed time E. In other embodiments, predicted interruptions can be mapped and incorporated into the prescription and the dynamic flow rate adjustment ahead of time and on the fly.

Similar to interruption X, the interruption Y at Y1 minutes results an 0 ml of volume accumulating from Y1 to Y2 minutes 246. Following interruption Y, pumping resumes at another recalibrated catch-up flow rate and volume accumulates as expected until the delivery's conclusion at E minutes. Because the system was programmed to adjust catch-up flow rate 216 to increase from F ml/min to G ml/min in order to complete the prescribed delivery on time, a second interruption Y will once again affect the total nutrition that will be delivered to the patient, absent another pump recalibration. As seen in upper chart 210, after the conclusion of Y interruption at Y2 minutes, the pump catch-up flow rate is recalibrated again and increased from G ml/min to H ml/min as shown by line 219. To determine just how much the pump need speed up to meet the volume and duration prescription, the flow rate H must be set at the same as the slope of line 248. It should be appreciated that B' ml of volume has been delivered as of interruption Y, and the slope line 248 can be calculated by subtracting B' from the total prescribed volume D over the time E minutes minus Y2 minutes.

Assuming the delivery does not experience anymore interruptions, and the flow rate H does not exceed any of the pump's maximum pre-set flow rates as discussed above, this second increased catch-up flow rate will result in the patient receiving the prescribed total volume over the prescribed delivery duration notwithstanding two disruptive interruptions.

Figure 3:
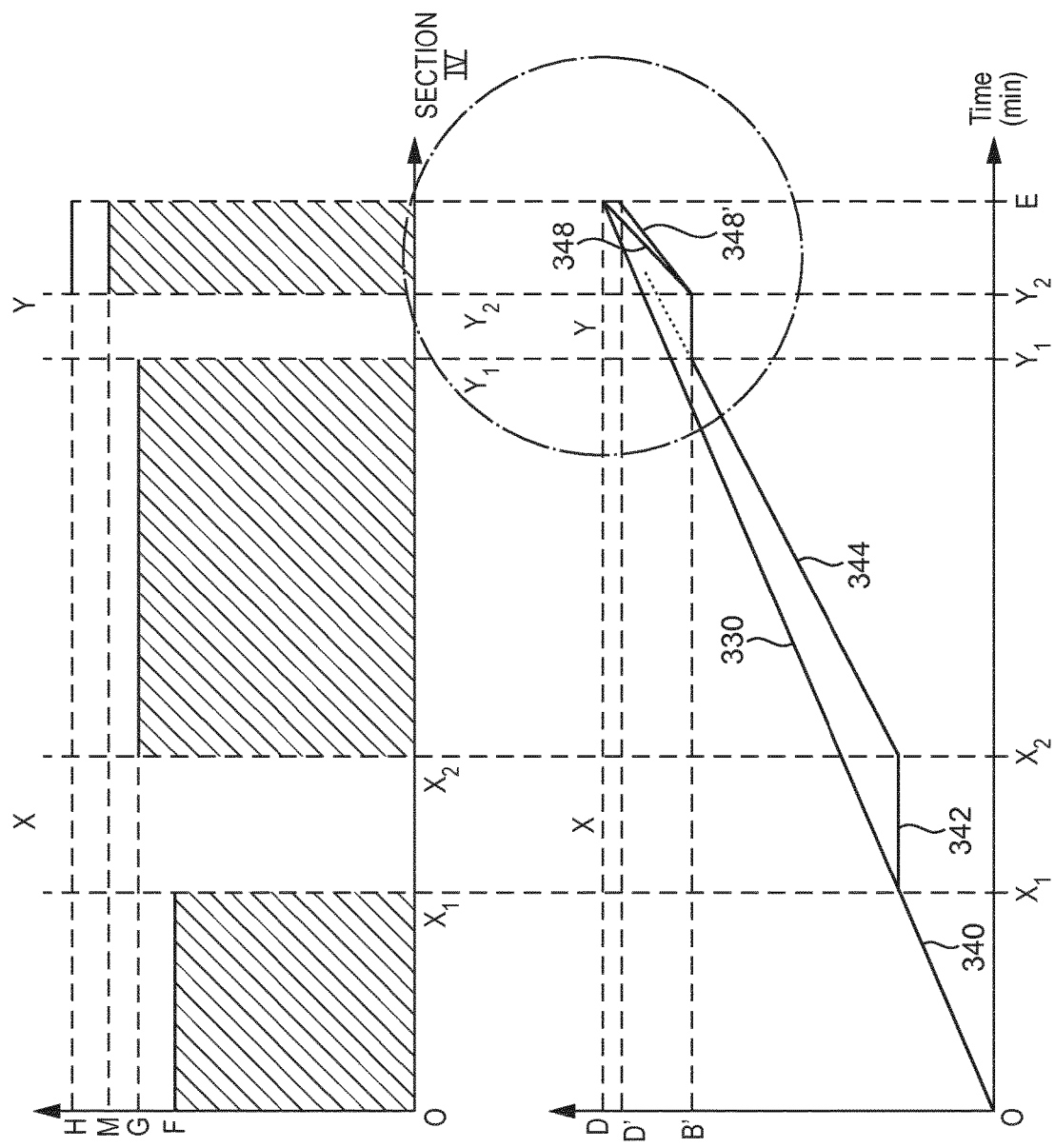
FIG. 3 shows flow rate and volume profiles of an automated enteral nutrition system of the present disclosure that undergoes interruptions or pauses in delivery, followed by catch-up flow rate adjustments subject to maximum catch-up flow rate limitations.

Referring now to FIG. 3, a further alternative embodiment of the above nutrition delivery example is illustrated and discussed. FIG. 3 includes a similar profile as FIG. 2, except a maximum flow rate limitation is placed on the pump at flow rate M ml/min. As can be seen in the upper chart 310, flow rate M falls between flow rate G ml/min and flow rate H ml/min. Therefore, the pump in this particular embodiment has been pre-programmed to prevent a flow rate of above M ml/min. It should be appreciated that the maximum set flow-rate can be doctor-specific, pump-specific, nutrition-specific, patient-specific, or any combination thereof. In various intermittent delivery regimens discussed below, a maximum intermittent threshold is alternatively defined and used.

After interruption X, and similar to the slope 244 of FIG. 2, the slope 344 of FIG. 3 equals G and results in the recalibration of the pump to increase its speed to still achieve the total prescription volume delivery within the prescribed duration assuming no more interruptions. However, when the interruption Y concludes at Y2 minutes on FIG. 3, the calculated slope 348 results in a flow rate H ml/min at 319 that exceeds the maximum flow rate M ml/min. Although it is most desirable to deliver 100% of the prescribed volume within the prescribed duration, real life situations will occasionally dictate that the duration and/or frequency of the delivery interruptions prevent catch-up pump flow rates from being sufficient to complete the prescription within safe operating limits. Therefore, in FIG. 3, the actual delivery line 348' must follow a slope of M ml/min as a maximum, and will therefore fall short of the total prescribed volume delivered. Rather than delivering D ml during the treatment, the maximum allowable volume delivered with flowrate M ml/min operating for E minus Y2 minutes is D' ml.

Figure 4:
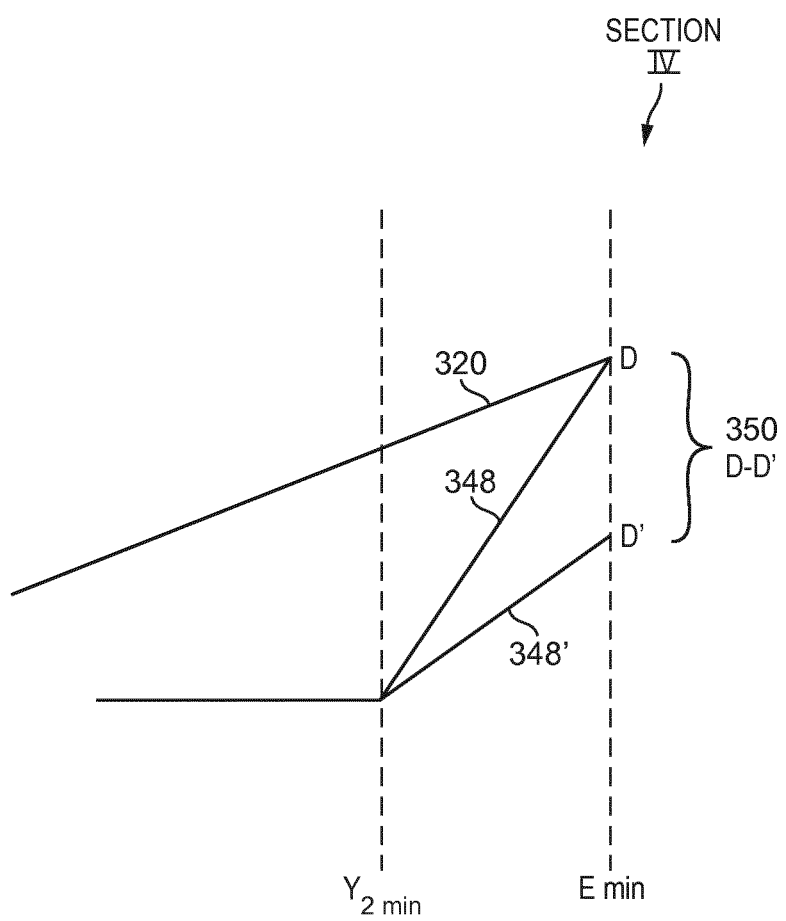
FIG. 4 shows the detail Section IV of FIG. 3.

The practical result of the maximum flow rate being reached is more easily illustrated in Section IV of FIG. 3, which can be seen in FIG. 4. Section IV shows the convergence of the calculated line 348 with best fit prescribed line 320, as well as the path of actual line 348' subject to the maximum flow rate M ml/min. Note: the slopes of these lines as illustrated in Section IV have been exaggerated for illustrative purposes and are not meant to track on scale with FIG. 3. After the Y interruption at Y2 minutes, the proposed or calculated slope 348 (matching with slope H ml/min of FIG. 3) provides the ideal fit to deliver the intended volume of nutrition D ml within the timeframe prescribed E minutes. However, because H ml/min is beyond the maximum flow rate M ml/min, the pump is reprogrammed to complete the delivery at the maximum of M ml/min, which is the slope of line 348'. As a result, the total amount of nutrition delivered D' ml is simply D minus D' ml short of the total prescription.

In various embodiments, the system is configured to display to the user or clinician both the proposed catch-up flow rate 348 and the maximum catch-up flow rate 348', and indicate to the user which of the flow rates is the actual pump operating flow rate. The system of various embodiments is configured to calculate and display on the user interface the amount of nutrition D minus D' that will not be delivered to the patient, but that was intended for delivery. In one embodiment, the system will determine the percentage of the total volume delivered vs volume prescribed, and display on the user interface what percent of the prescription was achieved. In other embodiments, the user interface will display what percentage has been achieved in real time, as well as what percentage will be achieved according to the current and/or maximum pump flow rates and the duration of delivery remaining. Some embodiments include the calculation of assuming no more interruptions in the calculation or projected prescription delivery percentage. Other embodiments may incorporate external parameters and factors in the calculation of the projected percentage prescription delivered, such as planned interruptions that may be specific to that patient.

In the FIGS. 3 and 4 scenario, the user interface of the system would graphically display to the patient the following parameters relating to actual volume delivered, projected volume delivered, actual flow rate, proposed flow rate based upon the time of the treatment. It should be appreciated that any and all of the below data can be conveyed on the user interface in any known format or design.

| Time | Proposed Flow rate | Max Flow Rate | Actual Flow Rate | Projected Volume | Actual Volume | Projected Percentage | Actual Percentage |
|------|--------------------|---------------|------------------|------------------|---------------|----------------------|-------------------|
| 0    | F                  | M             | F                | D                | 0             | 100%                 | 0%                |
| X1   | F                  | M             | 0                | D                | A             | 100%                 | (D-A/D)%          |
| X2   | G                  | M             | G                | D                | A             | 100%                 | (D-A/D)%          |
| Y1   | G                  | M             | 0                | D                | B'            | 100%                 | (D-B'/D)%         |
| Y2   | H                  | M             | M                | D                | B'            | 100%                 | (D-B'/D)%         |
| E    | M                  | M             | M                | D'               | D'            | (D-D'/D)%            | (D-D'/D)%         |

As seen in the table above, the Proposed Flow Rate shows the dynamically adjusting flow rates throughout six different milestones of the delivery: immediately at the start of delivery (0), beginning of interruption X (X1), end of interruption X (X2), beginning of interruption Y (Y1), end of interruption Y (Y2), and end of delivery. At the start of the delivery, the proposed flow rate is the prescribed flow rate until the end of an interruption, X2, at which point the proposed catch-up flow rate is adjusted to G. When a second interruption occurs, the proposed catch-up flow rate becomes H. Column three shows the max flow rate throughout the delivery, which is M. Column four lists the actual flow rate, which, during interruptions is zero, and which adjusts the proposed flow rate based upon any limitations from the max flow rate in column three. It should be appreciated that, since H exceeds M as seen on FIG. 3, the proposed flow rate at Y2 is excessive of the pump operating parameters, and therefore the actual flow rate is adjusted accordingly.

Column five shows the projected volume, which matches the prescribed volume D until it becomes evident to the pump that delivering all of the prescription is not feasible within the duration allowed, at which time it becomes D'. Actual volume delivered is shown in column six. It should be appreciated that, subject to the maximum flow rate M requiring the pump operate slower than the proposed flow rate H at Y2, the projected volume never reaches D, and therefore D' is the final volume of nutrition delivered to the patient. Columns seven and eight show the projected percentage of prescription that will be delivered by the end of feeding and the actual prescription delivered at the various times of the feeding, respectively.

Figure 5:
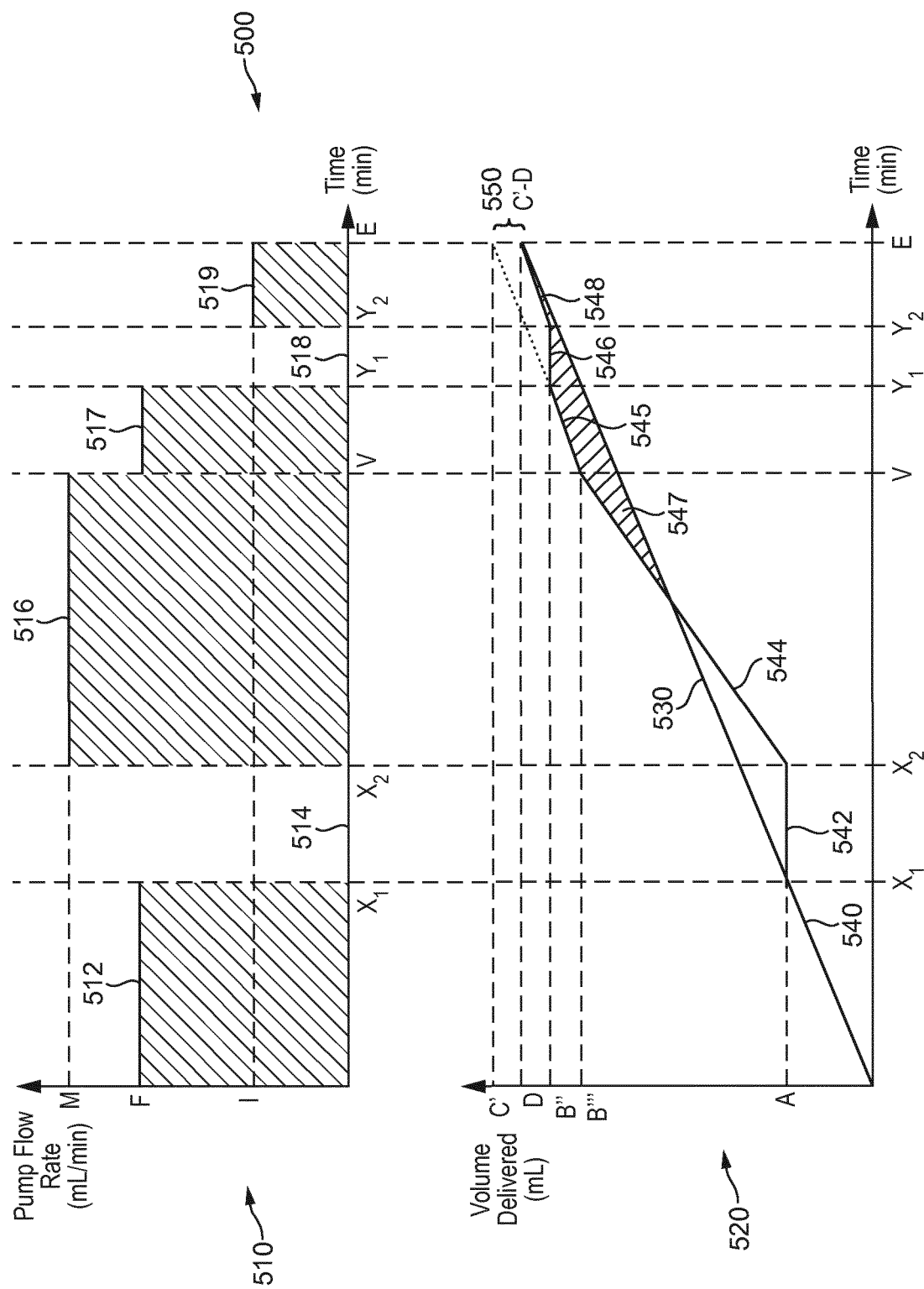
FIG. 5 shows flow rate and volume profiles of an automated enteral nutrition system of the present disclosure that undergoes interruptions or pauses in delivery, followed by over-delivery flow rate adjustments.

Referring now to FIG. 5, another alternative embodiment of the above nutrition delivery example is illustrated and discussed. FIG. 5 includes a similar profile as FIGS. 2 and 3, except the system sets the pump to its maximum flow rate after the first interruption, even though the extrapolation of such a maximum flow rate would result in over-delivery if maintained for the duration of the delivery. As can be seen in the upper chart 510, maximum flow rate M is set and achieved 516 after the first interruption X has concluded. Therefore, the pump in this particular embodiment has been pre-programmed to intentionally over-deliver fluids at the maximum pump flow rate M ml/min after an interruption. It should be appreciated that the over-delivery can be programmed to take place following and in the event of unexpected interruptions. In some embodiments, an expected interruption can be planned into the delivery, and therefore the pump's over-delivery at the max flowrate can also be planned or scheduled in the delivery regimen, and/or according to the clinical environment.

In the event of an over-delivery, whether as a result of a planned interruption or an unplanned interruption, the pump's flow rate is increased to the maximum flow rate M, as in FIG. 5. It should be appreciated that the over-delivery flow rate need not be the maximum flow rate M, but could also be some other flow rate which is higher than would be necessary to complete 100% of the delivery within the delivery duration of the prescription. In other words, while the extrapolation of a catch-up flow rate discussed above, absent subsequent unplanned interruptions, would result in close to or at the 100% delivery volume, the extrapolation of an over-delivery flow rate absent unplanned interruptions would result in more than 100% of the delivery volume. Delivering more than the prescription requires is undesirable. Therefore, the over-delivery flow rate embodiment includes pump programming that will taper off the pump flow rate from its over-delivery flow rate (whether maximum flow rate or something less) to a tapering flow-rate to arrive consistently at the 100% delivery volume in the required duration. The tapering flow-rate can be linear or it can be non-linear. In various embodiments, the tapering flow rate can still be an over-delivery flow rate based on the extrapolation discussion above. Such a tapering flow-rate, which would still extrapolate to over-deliver if kept linear for the remainder of the delivery duration, would be a desirable feature for delivery regimens which may expect or predict additional interruptions.

It should be appreciated that some systems enable the automatic adjustment of an over-delivery flow rate to accommodate future interruptions that are similar to historical ones. The system is capable of storing patient-specific data (either locally or through a known interconnected network and database system). From past deliveries, the system can become 'smart' to the specific patient to predict timing, duration, and frequency of potential unplanned interruptions. With such knowledge, or even the knowledge of data from a pool of typical patients (and not that specific patient), the prescriptions, over-delivery flow rates, catch-up flow rates, bolus feeding timings, planned stop durations, and override minimums and maximums can be adjusted proactively to adjust for future interruptions based on historical data.

In various alternative embodiments, an over-delivery flow rate or catch-up flow rate can be adjusted to accommodate for future interruptions similar to historical interruptions experienced during the same discrete continuous or intermittent feeding session. For example, if a feeding is scheduled for four hours and after the first hour, there were 15 minutes of total interruptions, the catch-up flow rate or over-delivery flow rate could be adjusted to not only make up for the 15 minutes of delay, but also to anticipate an additional 45 minutes of delay in the remaining three hours. The rate could be adjusted downward periodically (tapering flow rate) if these additional delays are not realized. It should be appreciated that the pump's incorporation of information into the catch-up flow rate or over-delivery flow rate calculations could be across a period of hours, days, weeks, or months. In some embodiments, the pump is set to accept information from historical data to become smart and in other embodiments the pump is set to be blind and not take into account its environment.

In various embodiments, the tapering flow rate is activated when the total nutrition volume or energy delivered is a certain percentage of the total prescribed nutrition volume or energy. For example, if 90% of the total nutrition volume or energy has been delivered, but only 80% of the duration of the delivery has elapsed, the pump can automatically slow the pump down to a linear or a non-linear tapering flow-rate profile so that the remaining 10% of total nutrition volume or energy is delivered smoothly over the remaining 20% of the prescribed delivery duration. It should be appreciated that, by using a tapering flow-rate profile, whether linear or non-linear, the prescription is still fully delivered as outlined and sudden increases or decreases of pump flow rate are avoided.

Referring again to FIG. 5, after interruption X, the slope 544 represents the over-delivery flow rate, which is triggered after interruption X has expired at time X2. As discussed above, the over-delivery flow rate can, but need not be equal to the maximum pump flow rate M discussed in previous embodiments above. In FIG. 5, the over-delivery flow rate 544 is set to be equal to the maximum pump flow rate M at 516 of upper chart 510. As can be seen in lower chart 520, the over-delivery flow rate 544 exceeds the slope of original flow rate F, and indeed more than makes up for the lost nutrition delivery caused by interruption X. After intended flow rate profile 530 intersects with over-delivery flow rate profile 544, a surplus amount of nutrition begins accumulating vs. the amount of nutrition expected to be delivered as of that particular time. The surplus amount of nutrition for any given time is illustrated by shaded area portion 547, and is equal to the difference between the actual volume delivered vs. time (544, 545, 546, 548) and the proposed linear volume delivered vs. time 530.

In FIG. 5, the pump is automatically set at its over-delivery flow rate from time X2 until time V. At time V minutes, the pump automatically decreases its flow rate to a first tapering flow rate 517, which in this embodiment is the same as the starting flow rate F. It should be appreciated that the tapering flow rate need not only be less than the over-delivery flow rate. In this embodiment, even the first tapering flow rate shows a profile line 545, which when extrapolated to time E minutes, would actually exceed the 100% delivery target D. Left unchanged and uninterrupted, that tapering flow rate would result in an over-delivery of C' minus D ml, which is not a desirable outcome. Therefore, to still achieve the 100% delivery, sometime between time Y1 and time E minutes, the tapering flow rate has to either decrease (linearly or non-linearly), or an interruption has to occur, or both. In various embodiments, the pump is programmed to dynamically monitor and adjust the flow rates of these tapering flow rates to prevent over-delivery.

Returning to FIG. 5, the tapering flow profile 545 is cut off when the pump experiences interruption Y at Y1 minutes and the pump flow rate goes to zero 518. As can be seen in lower chart 520, the accumulation of nutrition ceases as of the interruption Y1 at B" ml, and the surplus area 547 between the proposed and actual delivery curves decreases. After the interruption Y has concluded at Y2 minutes, a second tapering flow rate I is programmed into the pump to complete the nutrition delivery. As of the conclusion of the interruption Y, the remaining nutrition to be delivered is D−B" ml. The nutrition remaining and the time remaining have become short, and therefore the system programs the pump to automatically complete the delivery at 100% in the full duration E with tapering flow profile 548 at the rate of I ml per minute.

Figure 6:
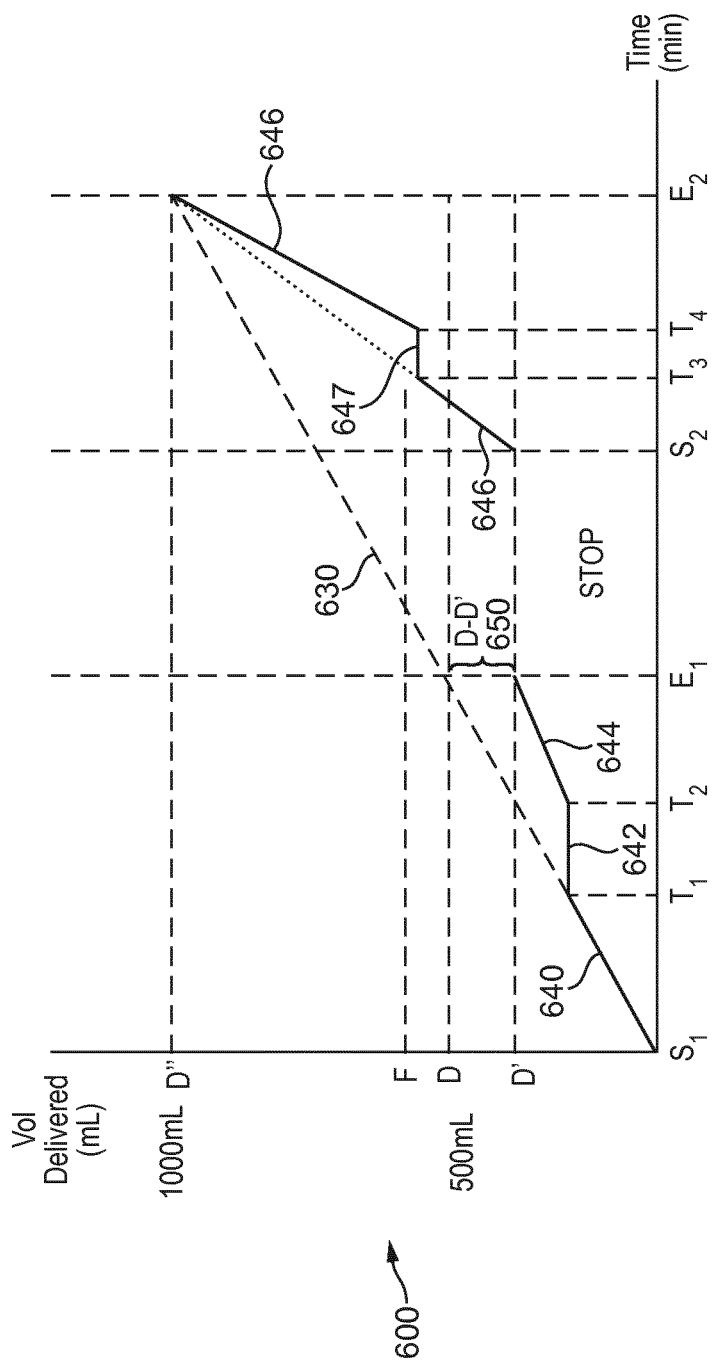
FIG. 6 shows the volume delivered profile of an intermittent nutrition system of the present disclosure.
Figure 7:
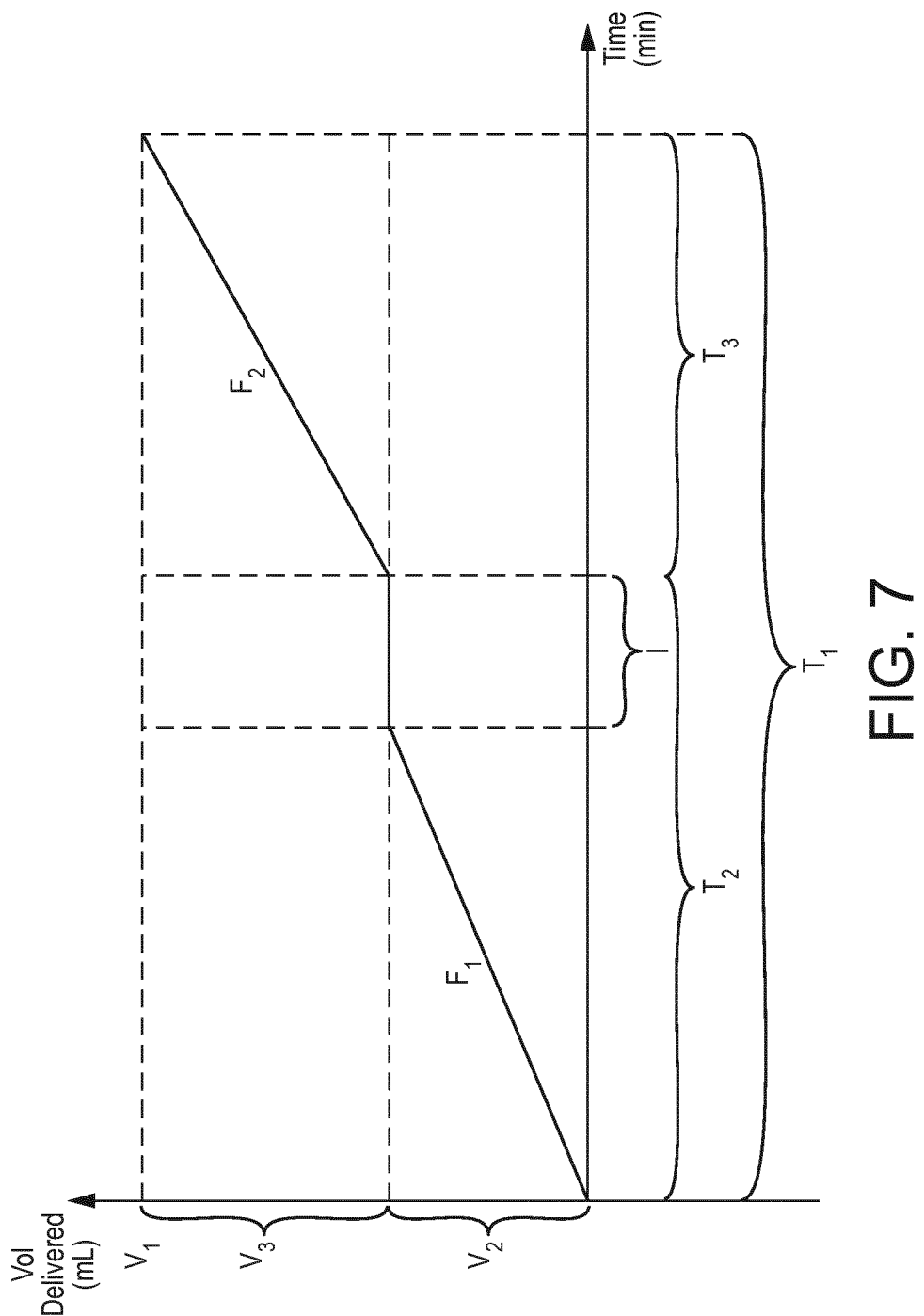
FIG. 7 shows a volume delivered profile of an enteral nutrition system that undergoes an interruption or pause in delivery.

Referring now to FIG. 6, an intermittent delivery system of one embodiment of the present disclosure is illustrated and described. The chart 600 of FIG. 6 shows two nutrition deliveries and a planned stop. The first delivery spans from time S1 minutes to time E1 minutes. The second delivery spans from time S2 minutes to time E2 minutes. Between the two deliveries, a planned stop spans from time E1 minutes to time S2 minutes. FIG. 6 illustrates what happens when an interruption (T1 min to T2 min) occurs during a first delivery S1 to E1. In the first delivery of this particular embodiment, the prescription has been set to deliver 500 ml (D ml) within E1 minutes. After starting flow profile 640, and interruption 642, a secondary flow rate 644 (whether a catch-up flow rate or otherwise) results in a shortfall of the delivery of D minus D1 ml 650 as of time E1.

In this particular intermittent delivery system 600, the second delivery (S2 to E2) is also originally prescribed to deliver 500 ml (D" minus D). Because there was a shortfall of delivery of D minus D1 ml 650 as of the end of the first delivery E1, the system is programmed to remember the shortfall and make up for it in the second delivery. For example, although the second delivery has a prescribed volume of 500 ml, its target flow rate in FIG. 6 has been adjusted to be 500 ml+the shortfall D−D' ml. Starting at time S2 minutes, the second delivery begins at flow profile 646 until interruption T3 to T4. It should be appreciated that flow rate 646, when extrapolated, will result in a total of 500 ml+(D−D') ml to be delivered in the second delivery. Even though the first delivery resulted in a shortfall, the two deliveries taken as a whole result in 1000 ml being delivered to the patient across two 500 ml prescriptions.

It should be appreciated that, if the deliveries of FIG. 6 were trifurcated instead of bifurcated, or if there were any number of deliveries and stops planned, any compensation for nutrition delivery shortfalls can be spread out across subsequent deliveries and need not be corrected immediately. Additionally, it should be appreciated that, in various embodiments, if a delivery has an over-delivery flow rate in anticipation of an interruption that never occurs, the surplus or over-delivery for one of the multiple intermittent deliveries can be mitigated by tapering off the volumes delivered for one or more of the subsequent deliveries.

In various embodiments, some or all of the information portrayed in the table above can be displayed on the user interface for a real-time view of feeding progress (volume and flow rate) and percentage of completion expected and achieved.

Figure 8:
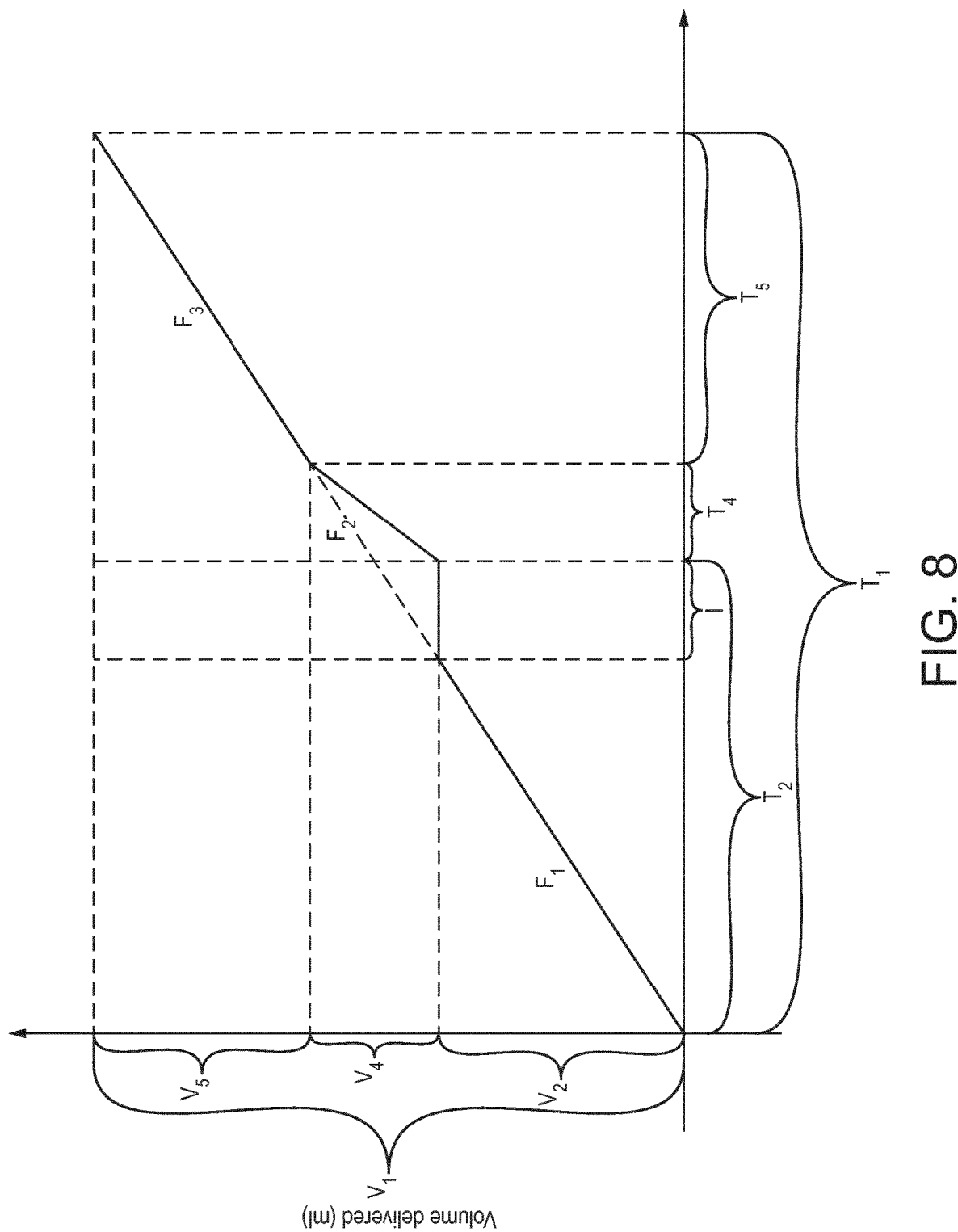
FIG. 8 shows flow rate and volume profiles of an automated enteral nutrition system of the present disclosure that undergoes interruptions or pauses in delivery, followed by catch-up flow rate adjustments based on a maximum allowable catch-up flow rate restriction.

In one embodiment, following an interruption (whether planned or unplanned), the pump controller increases the pump flow rate to the maximum allowable flow rate until the delivery is back on track with the planned delivery profile. Referring now to FIG. 8, one such embodiment is illustrated. A first nutrition parameter is the first nutrition volume to be delivered, V1 over a duration of the nutrition delivery (T1). Similar to embodiments discussed above, the controller calculates a first delivery flow rate (F1) of the pump based upon the first nutrition volume (V1) and the first duration (T1). Upon start of delivery, the controller instructions the pump to begin according to the first delivery flow rate (F1) until the event of an interruption of a second duration (I). After the interruption of the second duration (I) has concluded, the controller calculates a partial nutrition volume delivered (V2), a catch-up volume (V4) and a residual volume to be delivered (V5). It should be appreciated that, (V4) summed with (V5) equal the remaining volume to be delivered in order to complete the total (V1) nutrition delivery. Therefore, V1=V2+V4+V5.

The controller of this embodiment also calculates a partial time duration completed (T2), a catch-up time duration (T4), and a residual time duration (T5). Similar to the volumes of the profile, the overall time T1 is equal to the sum of: the partial time duration completed (T2), the catch-up time duration (T4), and the residual time duration (T5). Therefore, T1=T2+T4+T5.

In this embodiment, the controller also calculates a proposed delivery flow rate (F2) of the pump based upon a maximum allowable catch-up flow rate restriction, as discussed in other embodiments here. The controller also determines a residual flow rate (F3). In this embodiment, following the interruption, the pump is programmed to automatically ramp to the maximum allowable flow rate immediately, rather than an interim catch-up flow rate calculated as in other embodiments. The pump is operated at the maximum allowable flow rate (F2) until it reaches the original flow profile along the slope of (F1), at which point it is "back on track". Once the flow profile is back on track, the pump speed is reduced to a residual flow rate (F3), which in one embodiment, is the same as the first delivery flow rate (F1). In an embodiment, the controller calculates the residual flow rate (F3) based upon the residual volume (V5) and the residual time (T5), wherein F3=V5/T5. In various embodiments, the proposed delivery flow rate (F2) is greater than the residual flow rate (F3). In an embodiment, the proposed delivery flow rate (F2) is equal to the maximum allowable catch-up flow rate restriction. In an embodiment, the catch-up time T4=[V1−V2−F1*(T1−T2)]/(F2−F1).

Figure 9:
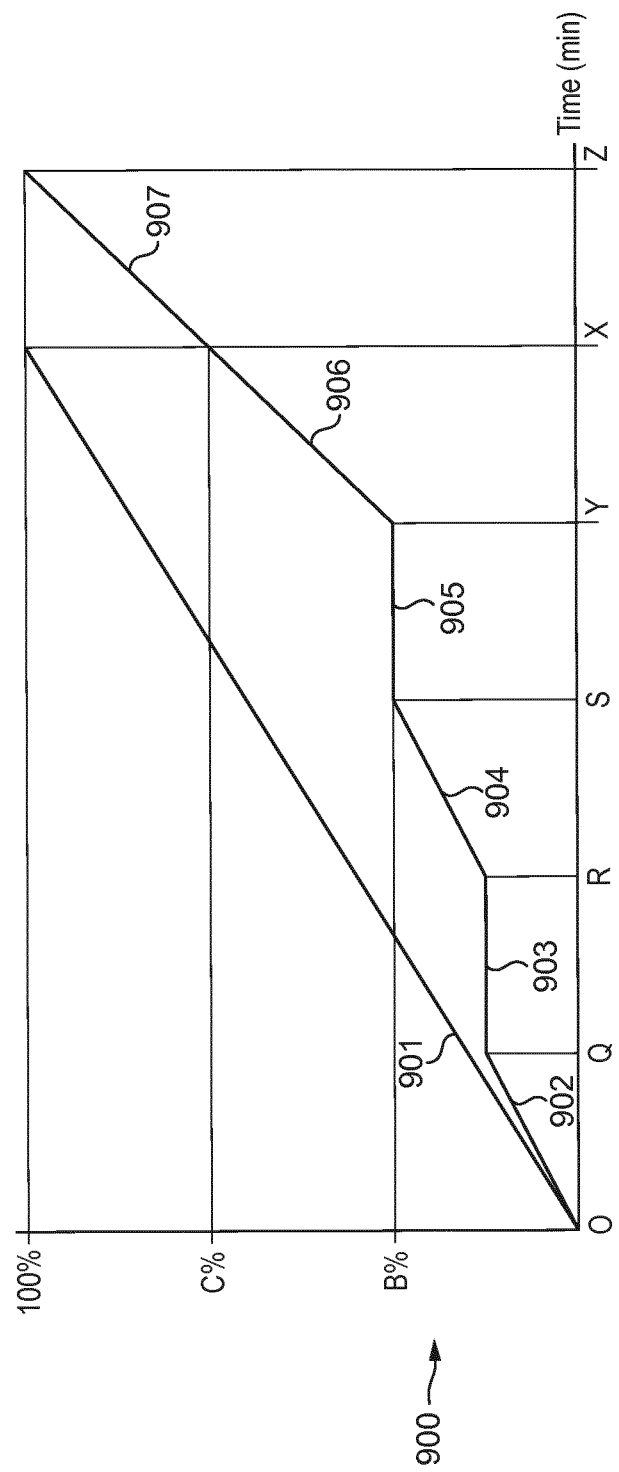
FIG. 9 shows flow rate and volume profiles of an automated enteral nutrition system of the present disclosure that undergoes interruptions or pauses in delivery, followed by catch-up flow rate adjustments based on a maximum allowable catch-up flow rate restriction, followed by an extension of the total delivery time to deliver 100% of the nutrition prescribed.

In another embodiment discussed above and illustrated in FIG. 9, the pump will provide an extended delivery option to achieve full prescription delivery when an interruption will result in the failure to achieve 100% prescription delivery within the allotted time, even when the pump is operating at its maximum allowable catch-up flow rate. Referring now to FIG. 9, a delivery profile 900 is illustrated, showing the percent of total prescribed nutrition along the Y axis and the time elapsed in the delivery along the X axis. Line 901 illustrates a line whose slope is equal to the planned flow rate (nutrition delivered over time elapsed) for the delivery at its start time=0. The slope of line 902 represents the actual flow rate of the pump from time=0 until time=Q minutes. That the initial actual flow rate 902 is less than the planned delivery flow rate 901 is irrelevant to this example. At Q minutes of the delivery, there is an interruption that lasts a duration of R minutes minus Q minutes. During this interruption, the slope of line 903 is zero, thus indicating the pump is stopped.

Upon resumption of the delivery, the pump's flow rate is increased as illustrated by the slope of line 904 between time R minutes and time S minutes. At S minutes of the delivery, a second interruption occurs 905 for a duration of Y minus S minutes. It should be appreciated that any number of interruptions are contemplated prior to the extended delivery operation embodiment discussed here. At time Y minutes of the delivery, when the interruption has concluded, the pump system calculates that the maximum allowable catch-up flow rate. In the illustrated embodiment, the slope of line 906 represents the maximum allowable catch-up flow rate. At time Y, the pump system recognizes that only B % of the total 100% nutrition has been delivered. The pump system also recognizes that the allotted time for the entire delivery is X minutes. As seen graphically in FIG. 9, at the time of conclusion of the second interruption 905, there exists only X minus Y minutes remaining in the allotted delivery time. As is also evident from the figure, even when the pump is operated at its maximum allowable catch-up flow rate 906, the most nutrition that can be delivered by time X is only C % of the total 100%.

Accordingly, in this and other contemplated embodiments, the pump system: (1) calculates at time Y that the maximum allowable catch-up flow rate 906 will not result in 100% nutrition delivery by allotted time X minutes; and (2) calculates a time Z minutes at which point 100% of the nutrition would be delivered with the pump operating under the maximum allowable catch-up flow rate, or any other suitable flowrate programmed by the clinician. Upon calculation of required delivery extension time Z minutes, the pump system of various embodiments provides the option to the patient or clinician to extend the delivery by the required duration of Z minus X minutes in order to deliver the full 100% of the nutrition to the patient.

Various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A pump system for delivering an enteral nutrition composition, the pump system comprising:
 a pump, an input device, a controller, a memory device and a processor, the processor configured to execute instructions stored on the memory device to cause the controller to:
 via the input device, enable a user to input a first nutrition parameter and a first duration of a nutrition delivery (T1), wherein the first nutrition parameter is a first nutrition volume to be delivered (V1);
 calculate a first delivery flow rate (F1) of the pump based upon the first nutrition volume (V1) and the first duration (T1);

start the pump according to the first delivery flow rate (F1);

stop the pump in the event of a pump interruption of a second duration, wherein the second duration is an interruption duration (I);

determine if the interruption duration exceeds an interruption duration threshold;

if the interruption duration does not exceed the interruption duration threshold, continue operating the pump according to the first delivery flow rate; and if the interruption duration exceeds the interruption duration threshold, after the conclusion the pump interruption:

calculate a partial nutrition volume delivered (V2) and a remaining nutrition volume to be delivered (V3), wherein: V1=V2+V3;

calculate a partial time duration completed (T2) and a remaining time duration (T3), wherein T1=T2+T3; and calculate a proposed delivery flow rate (F2) of the pump based upon the remaining nutrition volume to be delivered and the remaining time duration, wherein the instructions include a maximum allowable flow rate of the pump;

determine if the proposed delivery flow rate exceeds the maximum allowable flow rate; and if the proposed delivery flow rate does not exceed the maximum allowable flow rate, resume the pump according to the proposed delivery flow rate, wherein the proposed delivery flow rate of the pump is higher than the first delivery flow rate of the pump.

2. The pump system of claim 1, wherein the first delivery flow rate of the pump is calculated based additionally on at least one of a first nutrition energy target to be delivered (E1) or a first nutrition protein target to be delivered (P1).

3. The pump system of claim 1, which includes calculating a proposed nutrition regimen for intermittent feeding.

4. A method for controlling a pump for delivering an enteral nutritional composition, the method comprising the steps of:

receiving a first nutrition parameter and a first duration of nutrition delivery (T1) defining at least a portion of a prescription, wherein the first nutrition parameter is a first nutrition volume to be delivered (V1);

starting the pump with a first delivery flow rate calculated based upon the first nutrition volume to be delivered (V1) and the first duration of nutrition delivery (T1) of the prescription;

stopping the pump in the event of a pump interruption of a second duration, wherein the second duration is an interruption duration;

determining if the interruption duration exceeds an interruption duration threshold:

if the interruption duration does not exceed the interruption duration threshold, continue operating the pump according to the first delivery flow rate; and if the interruption duration exceeds the interruption duration threshold:

after the second duration, calculate a proposed delivery flow rate based upon a duration of partial time remaining (TR) from the first duration of nutrition delivery of the prescription and a partial volume of the nutrition delivered (VR) from the first nutrition volume of the prescription;

determining if the proposed delivery flow rate exceeds a maximum allowable flow rate of the pump;

wherein, if the proposed delivery flow rate does not exceed the maximum allowable flow rate, restarting the pump after the pump interruption has concluded at the proposed delivery flow rate for the duration of partial time remaining or until a subsequent interruption, wherein the proposed delivery flow rate of the pump is higher than the first delivery flow rate of the pump, and wherein the proposed delivery flow rate is calculated to enable the pump to deliver the first nutrition volume within the first duration of nutrition delivery of the prescription notwithstanding the pump interruption.

5. The method of claim 4, wherein the first delivery flow rate of the pump is calculated based additionally on at least one of a first nutrition energy target to be delivered (E1) or a first nutrition protein target to be delivered (P1).

6. The method of claim 4, which includes calculating a proposed nutrition regimen for intermittent feeding.

7. The method of claim 4, which includes defining the maximum allowable flow rate of the pump.

8. A non-transitory machine-readable storage medium comprising machine-readable instructions for causing a processor to execute a method for use with a medical device and an associated pump to automate enteral nutrition delivery, the method comprising:

receiving a first nutrition parameter and a first duration of nutrition delivery (T1) defining at least a portion of a prescription, wherein the first nutrition parameter is a first nutrition volume to be delivered (V1);

starting the pump at a first delivery flow rate calculated based upon the first nutrition volume to be delivered (V1) and the first duration of nutrition delivery (T1) of the prescription;

stopping the pump in the event of a pump interruption of a second duration, wherein the second duration is an interruption duration;

determining if the interruption duration exceeds an interruption duration threshold:

if the interruption duration does not exceed the interruption duration threshold, continue operating the pump according to the first delivery flow rate; and if the interruption duration exceeds the interruption duration threshold, after the second duration has concluded, calculate a proposed delivery flow rate based upon a duration of partial time remaining (TR) from the first duration of nutrition delivery of the prescription and a partial volume of the nutrition delivered (VR) from the first nutrition volume of the prescription; and comparing the proposed delivery flow rate with a maximum allowable flow rate:

if the proposed delivery flow rate exceeds the maximum allowable flow rate:

restarting the pump at the maximum allowable flow rate; and calculating and displaying the maximum allowable flow rate on a display device associated with the pump; and if the proposed delivery flow rate does not exceed the maximum allowable flow rate, restarting the pump at the proposed delivery flow rate, wherein the proposed delivery flow rate of the pump is higher than the first delivery flow rate of the pump.

9. The non-transitory machine-readable storage medium of claim 8, wherein the first delivery flow rate of the pump is calculated based additionally on a first nutrition energy target to be delivered (E1).

10. The non-transitory machine-readable storage medium of claim 9, further comprising the step of defining an energy density of the prescription.

11. The non-transitory machine-readable storage medium of claim 8, wherein the first delivery flow rate of the pump is calculated based additionally on a first nutrition protein target to be delivered (P1).

12. The non-transitory machine-readable storage medium of claim 11, further comprising defining a protein ratio of the prescription.

13. The non-transitory machine-readable storage medium of claim 8, further comprising defining at least one maximum allowed intermittent feeding parameter.

14. The non-transitory machine-readable storage medium of claim 13, wherein the maximum allowable flow rate and the at least one maximum allowed intermittent feeding parameter can be modified by a user.

* * * * *